United States Patent
Aizenberg et al.

(10) Patent No.: US 9,651,548 B2
(45) Date of Patent: May 16, 2017

(54) SELF-REGULATING CHEMO-MECHANO-CHEMICAL SYSTEMS

(71) Applicant: President and Fellows of Harvard College, Cambridge, MA (US)

(72) Inventors: Joanna Aizenberg, Boston, MA (US); Ximin He, Cambridge, MA (US); Michael Aizenberg, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 245 days.

(21) Appl. No.: 14/268,561

(22) Filed: May 2, 2014

(65) Prior Publication Data
US 2014/0349870 A1 Nov. 27, 2014

Related U.S. Application Data

(63) Continuation of application No. PCT/US2012/063595, filed on Nov. 5, 2012.

(60) Provisional application No. 61/555,965, filed on Nov. 4, 2011.

(51) Int. Cl.
*G01N 33/543* (2006.01)
*B81B 3/00* (2006.01)
(Continued)

(52) U.S. Cl.
CPC ...... *G01N 33/54366* (2013.01); *B01L 3/5027* (2013.01); *B81B 3/0032* (2013.01);
(Continued)

(58) Field of Classification Search
CPC .................. G01N 33/54366; G01N 29/022
See application file for complete search history.

(56) References Cited

U.S. PATENT DOCUMENTS

| 8,927,464 B2 | 1/2015 | Aizenberg et al. |
| 2007/0077396 A1 | 4/2007 | Aizenberg et al. |

FOREIGN PATENT DOCUMENTS

| EP | 2128598 A1 | 12/2009 |
| JP | 2001091491 A | 4/2001 |

(Continued)

OTHER PUBLICATIONS

Cohen, M. A. et al., "Emerging Applications of Stimuli-Responsive Polymer Materials," Nature Materials, vol. 9, pp. 101-113 (Feb. 2010).

(Continued)

*Primary Examiner* — Sean E Conley
*Assistant Examiner* — Matthew Krcha
(74) *Attorney, Agent, or Firm* — Wilmer Cutler Pickering Hale and Dorr LLP

(57) ABSTRACT

A chemo-mechano-chemical ($C_1$-M-$C_2$) system includes a base supporting an actuatable structure, said structure comprising a functionalized portion and being embedded in an environmentally responsive gel capable of volume change in response to an environmental stimulus; a first fluid layer disposed over the base and in contact with the actuatable structure, said first fluid layer comprising the environmentally responsive gel; and a second fluid layer in contact with the actuatable structure, wherein the layers are positioned such that the functionalized portion is in contact with the second layer in a first relaxed state and in contact with the first layer in a second actuated state and wherein the functionalized portion interacts with at least one of the layers to provide a chemical or physical response.

23 Claims, 29 Drawing Sheets

(51) Int. Cl.
| | |
|---|---|
| B01L 3/00 | (2006.01) |
| G05D 23/02 | (2006.01) |
| C12P 1/02 | (2006.01) |
| C12P 3/00 | (2006.01) |
| C12Q 1/66 | (2006.01) |
| G01N 33/58 | (2006.01) |
| G01N 33/86 | (2006.01) |

(52) U.S. Cl.
CPC ........ *C12P 1/02* (2013.01); *C12P 3/00* (2013.01); *C12Q 1/66* (2013.01); *G01N 33/582* (2013.01); *G01N 33/86* (2013.01); *G05D 23/021* (2013.01); *B01L 2300/0636* (2013.01); *B01L 2300/0877* (2013.01); *B01L 2300/1822* (2013.01); *B01L 2400/084* (2013.01); *B81B 2201/058* (2013.01)

(56) References Cited

FOREIGN PATENT DOCUMENTS

| WO | WO 2009070796 A1 * | 6/2009 | ......... B81C 1/00206 |
|---|---|---|---|
| WO | WO-2009070796 A1 | 6/2009 | |

OTHER PUBLICATIONS

He, X. et al., "Synthetic homeostatic materials with chemo-mechano-chemical self-regulation," Nature Letters, vol. 487, 25 pages (including supplemental) (Jul. 12, 2012).

Hong, Y. et al., "Biomimetic behavior of synthetic particles: from microscopic randomness to macroscopic control," Physical Chemistry Chemical Physics, vol. 12, pp. 1423-1435 (2010).

Kim, P. et al., "Hydrogel-Actuated Integrated Responsive Systems (HAIRS): Moving Towards Adaptive Materials," Current Opinion in Solid State and Materials Science, vol. 15, Issue 6, pp. 236-245 (Dec. 2011).

Kim, P. et al., "Microbristle in Gels: Toward All-Polymer Reconfigurable Hybrid Surfaces," Soft Matter. vol. 6, No. 4, pp. 750-755, 7 pages (Feb. 21, 2010).

Lutz, J.-F. and Hoth, A. "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, vol. 39, No. 2, pp. 893-896 (2006).

Okano, T. et al., "Thermally on-off Switching Polymers for Drug Permeation and Release," J. Controlled Rel., vol. 11, No. 1-3, pp. 255-265 (Jan. 1990).

Philippova, O. E. et al., "p-H Responsive Gels of Hydrophobically Modified Poly(acrylic acid)," Macromolecules, vol. 30, No. 26, pp. 8278-8285 (Dec. 29, 1997).

Schild, H. G., "Poly(*N*-isopropylacrylamide): Experiment, Theory and Application," Prog. Polym. Sci., vol. 17, No. 2, pp. 163-249 (1992).

Ward et al., "Thermoresponsive Polymers for Biomedical Applications," Polymers, vol. 3, 2011 (pp. 1215-1242).

International Search Report and Written Opinion issued on Jun. 25, 2013 in the International Application: PCT/US2012/063595, filed Nov. 5, 2012, 9 pages.

* cited by examiner

FIG. 7A
FIG. 7B
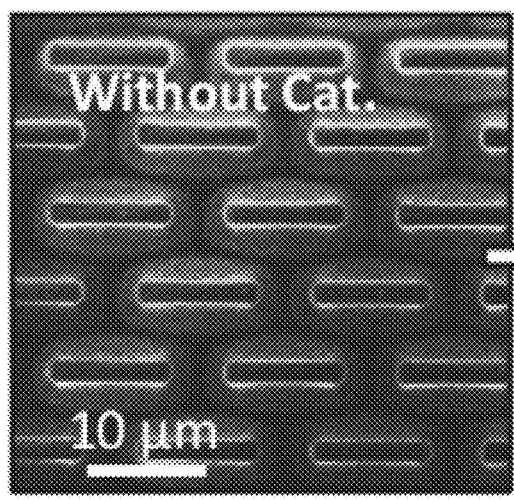
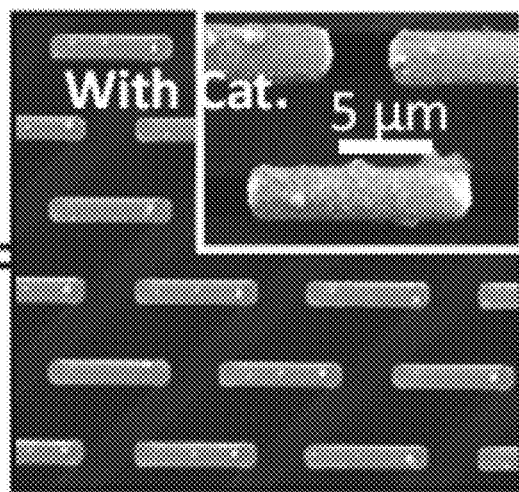
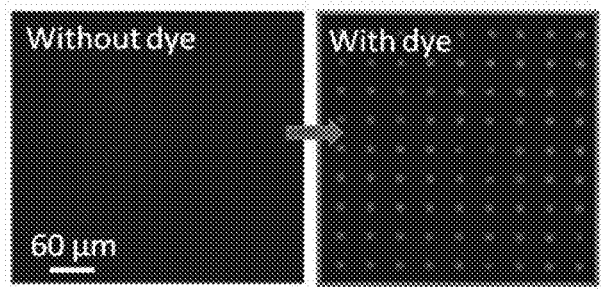
FIG. 7C

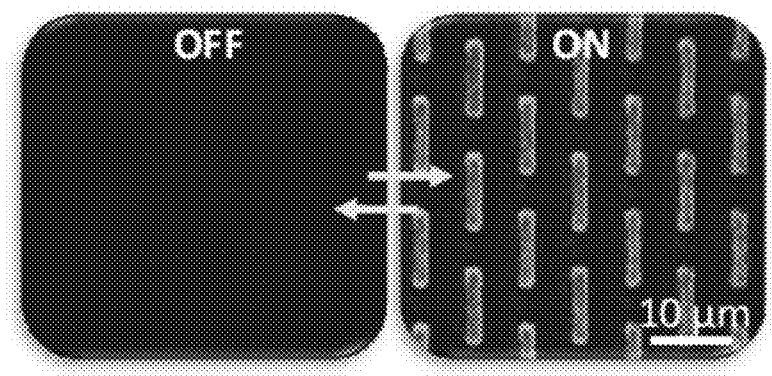
FIG. 12A         FIG. 12B
FIG. 13
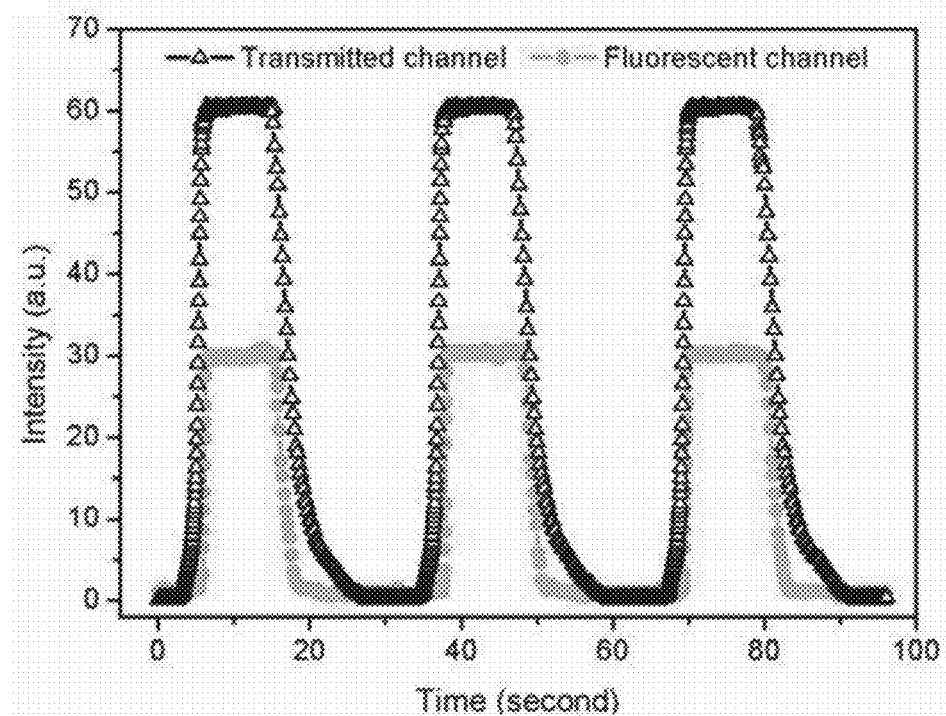

SELF-REGULATING CHEMO-MECHANO-CHEMICAL SYSTEMS

REFERENCE TO PRIOR APPLICATIONS

This is a continuation application of International Patent Application No. PCT/US2012/063595 filed Nov. 5, 2012 and entitled "Self-Regulating Chemo-Mechano-Chemical Surfaces," which claims priority to U.S. application Ser. No. 61/555,965, filed Nov. 4, 2011 and entitled "Self-Regulating Chemo-Mechano-Chemical Surfaces," which are incorporated in their entirety by reference.

GOVERNMENT RIGHTS

The present invention was made with United States government support under Award No.: DE-SC0005247 awarded by the Department of Energy and NSF Award #1124839 awarded by the National Science Foundation. The United States government has certain rights in this invention.

INCORPORATION BY REFERENCE

All patents, patent applications and publications cited herein are hereby incorporated by reference in their entirety in order to more fully describe the state of the art as known to those skilled therein as of the date of the invention described herein.

SEQUENCE LISTING

The instant application contains a Sequence Listing which has been submitted in ASCII format via EFS-Web and is hereby incorporated by reference in its entirety. Said ASCII copy, created on Jan. 4, 2013, is named 426973WO.txt and is 820 bytes in size.

TECHNICAL FIELD

The field of invention relates generally to an adaptive chemo-mechano-chemical smart device. The invention also relates to the use of a chemo-mechano-chemical smart device in thermal regulation, environmental remediation, energy conversion, microfluidics, chemical sensing and control, and optical applications, among others.

BACKGROUND

Interconversion of mechanical and chemical energy lies at the core of nearly all adaptive responses exhibited by living systems. From the simplest bacteria to complex mammals, survival is dependent upon the organism's ability to extract meaningful signals from the environment and to respond via sophisticated mechanochemical receptors and chemical signaling. Our hearing ability via mechanosensory hair cells and the neural system, the muscle contraction via ATP-regulated power strokes of myosin motors, and the rotary motion of flagella using molecular motors in the cell are examples of such interconversion.

The concept of a system, which converts chemical energy to mechanical energy and vice versa, is of basic interest; but of further consequence is a system which connects two chemistries with an intermediate mechanical step: a chemo-mechano-chemical or C-M-C system, as in the case of ATP synthase. Importantly, what distinctly sets biological mechanochemical systems apart from artificial materials systems such as sensors and actuators is their ability to self-regulate via cyclic energy flow within feedback loops; a mechanical stimulus generates a chemical signal that in turn drives another mechanical response, etc. The human body utilizes feedback mechanisms to promote homeostasis and maintain its core temperature, blood, pH, and sugar/glucose levels, all facilitated by information exchange between blood vessel or organs as a receptor, brain as a control center, and muscles, insulin or other components as effectors. For example, the human body also has a remarkable capacity for precisely regulating its core temperature within less than 1° C. by utilizing feedback mechanisms, which include sensing and actuating, e.g. shivering, vasoconstriction, neurotransmitter secretion, perspiration, etc. to achieve homeostasis. Indeed, the entire Earth functions as a vast homeostatic superorganism comprised of countless feedback loops involving everything from climate conditions to adaptation/extinction of species over time.

In synthetic systems, chemical-mechanical transduction has been approached from two separate angles: chemo-mechanical (C→M) and mechano-chemical (M→C) pathways. Examples include the nanomechanical biomolecular detector, responsive polymer-based actuators and synthetic molecular transporters as C→M devices, and damage sensors and shear-induced optics as M→C devices; no such synthetic systems provide for a feedback mechanisms that involve both C→M and M→C modes to lead to a self-regulated C→M→C transduction, which is fundamental to regulatory functions that would allow the system to self-regulate and autonomously control its state (temperature, pH, pressure, metabolite levels, etc.)

The development of sensitive and high-throughput biomolecule separation assays capable of rapid non-destructive sorting is crucial for advancing both medical diagnostics and biological discovery, such as cell counting, sorting, biomarker detection and protein engineering. Traditional protein separation and purification techniques include affinity chromatography, size exclusion, ion-exchange, and counter-current chromatography, often performed with a fast-performance liquid chromatograph (FPLC). These methods work with large amounts of target material (μg-mg) and typically require modification of the target proteins with an affinity tag (ie. His, FLAG) or several rounds of purification, sometimes lasting several days. However, to perform rapid tests with sub-microliter sample volumes, miniaturized devices with comparable or higher efficiency would be desirable. While significant progress has been made on microdevices for either separation or detection, current devices have the following limitations: 1) the target molecules need to be modified with handles such as fluorophores or streptavidin, which can change the native functions of the protein and preclude analysis of unmodified samples; 2) the detection and separation methods require the use of electric fields, IR, or magnetic fields; 3) the release of the target molecules necessitates destructive strategies such that the separation device can only be effectively used once (or a limited number of times); and 4) in some cases, biomolecules of similar sizes or similar chemical nature (including charge, conformation, hydrophobicity, etc.) are not able to be well-discriminated. Recently reported devices configured for gentle capture-and-release require washing and elution steps to separate targets from non-targets; however, devices that perform concerted capture, separation, and release which do not need extensive washing and elution are not available. As a result, cost-efficient, easy-to-implement microdevices capable of catching unmodified biomolecules and releasing them in a way that retains native function are highly desired and would allow collection of target molecules for downstream quantitative analysis or further use.

SUMMARY

In one aspect, self-regulating chemo-mechano-chemical surfaces are provided. Chemically functionalized tips of hydrogel-actuated microstructures are reversibly transferred in and out of a reagent layer thereby turning on and off a chemical reaction. This design provides a customizable and tunable device, providing a means of mechanically linking previously non-relatable chemical inputs and outputs.

Self-Modulated Adaptively Reconfigurable Tunable Surfaces (SMARTS) include nano- or microstructures with appropriately functionalized (chemically or physically) tips embedded in a hydrogel (hydrogel-actuated integrated responsive structures, HAIRS), the hydrogel further immersed in a biphasic liquid where a first phase includes chemical reagents and a second phase is water or other swelling liquid (or vice versa, where applicable). This dynamic system incorporates the movement of "skeletal" high-aspect-ratio microstructures (posts, blades, etc.) by a polymeric "muscle" provided by the swelling/contracting capabilities of the hydrogel in which the microstructures are embedded. In some embodiments, the layers are arranged vertically, one stacked over the other. The system can be also designed horizontally with these two layers positioned side-to-side.

The actuation of HAIRS is synchronized with the on/off switching of the chemical reaction, via the interplay of the motion of HAIRS and reaction-induced environment change. The actuation can be induced by a chemical reaction taking place in either layer or even by an external chemical or physical stimulus. A variety of external stimuli are capable of inducing reversible molecular changes in the gel, which powers the concerted actuation of the microstructures.

Incorporation of carefully designed feedback mechanisms ($C \leftrightarrows M$) into these systems has enabled continuous chemical, thermal and mechanical energy interconversions, resulting in autonomous, self-sustained materials.

The chemo-mechano-chemical ($C_1$-M-$C_2$) system exhibits the capability of regulated energy interconversion via three key components: Input signal→Control center: Mechanical movement→Output signal, in the form of both single direction and feedback loop. Both the input and output can be diverse types of energy, leading to a large variety of the functions and applications. The systems are capable of regulating temperature, pressure and motion of the device and its environs. The devices can function as thermostats, temperature-regulated construction elements, microfluidic devices, switches, cargo transport and in thermovoltaics.

SMARTS is also capable of functioning in delicate, biologically-relevant environments allowing it to regulate complex, multi-component biochemical processes. This greatly expands the scope of SMARTS and demonstrates the utility of this broad-based platform for biomedical applications and biological studies.

In one aspect, a chemo-mechano-chemical ($C_1$-M-$C_2$) system includes a base supporting an actuatable structure, said structure comprising a functionalized portion and being embedded in an environmentally responsive gel capable of volume change in response to an environmental stimulus; a first fluid layer disposed over the base and in contact with the actuatable structure, said first fluid layer comprising the environmentally responsive gel; and a second fluid layer in contact with the actuatable structure, wherein the layers are positioned such that the functionalized portion is in contact with the second layer in a first relaxed state and in contact with the first layer in a second actuated state and wherein the functionalized portion interacts with at least one of the layers to provide a chemical or physical response.

In one or more embodiments, the chemical or physical response provides the environmental stimulus that triggers a volume change in the environmentally responsive gel so that the system is self-regulating.

In one or more embodiments, the system further includes an external source of environmental stimulus capable of triggering a volume change in the environmentally responsive gel.

In one or more embodiments, the first and second layers are vertically arranged, or the first and second layers are horizontally arranged.

In one or more embodiments, the second fluid is a gas and the chemical or physical response takes place in the first fluid.

In one or more embodiments, the gel is a hydrogel, or a lyogel or an organogel.

In one or more embodiments, the stimulus is a change in temperature due to an exothermic reaction.

In one or more embodiments, the stimulus is a change in temperature due to an endothermic reaction.

In one or more embodiments, the stimulus is one or more from the following parameters: pH, heat, light, electric field, ultrasound, magnetic field, pressure, ion concentration, organic molecule concentration, biomolecule concentration or a combination thereof.

In one or more embodiments, the first and second layers are arranged in a static configuration.

In one or more embodiments, the system comprises a microfluidic system and the first and second fluids liquids flow in laminar pathways through the structures embedded in the environmentally responsive gel.

In one or more embodiments, the functionalized portion comprises a catalyst and one of the first or second layers comprises reagents that react when brought in contact with the catalyst.

In one or more embodiments, the gel, the structure and functionalized portion are selected to provide a preselected actuation characteristic.

In one or more embodiments, the functionalized portion interacts with reactants present in the second fluid layer to provide a chemical or physical response.

In one or more embodiments, the structures comprise a first upper portion comprising a first reactant and a second lower portion comprising a second reactant, wherein the structures are positioned and arranged such that the structures are spaced apart in the first relaxed state and the first and second reactants of neighboring structures contact each other in the second actuated state bringing the first and the second reactant in contact to provide a chemical or physical response.

In one or more embodiments, the system comprises a first set of structures comprising a first reactant and a second set of structures comprising a second reactant, wherein the structures are positioned and arranged such that the first set and second set of structures are spaced apart in the first relaxed state and the first and second reactants of neighboring first and second set of structures contact each other in the second actuated state to provide a chemical or physical response.

In one or more embodiments, the system further comprises a third reaction layer disposed between the first layer comprising the environmentally responsive gel and the second layer comprising the functionalized portion in the first relaxed state, wherein the third reaction layer comprises reactants capable of being catalyzed by the functionalized portion to provide a chemical or physical response.

In one or more embodiments, the system couples the mechanical action of a temperature-responsive gel with temperature generation occurring as the chemical or physical response to provide a self-powered, self-regulated oscillating system.

In one or more embodiments, the functionalized portion comprises an enzyme and the enzyme interacts with at least one of the layers to provide a biochemical response.

In one or more embodiments, the functionalized portion comprises a dye and the dye is moveable between the first and second layers to reversibly display or quench the dye.

In one or more embodiments, the functionalized portion comprises an aptamer and the aptamer is movable between the first and second layers to reversibly bind and release a target molecule.

In one or more embodiments, the system regulates temperature, or generates gas or light.

In another aspect, a method of chemo-mechano-chemical ($C_1$-M-$C_2$) actuation includes providing a chemo-mechano-chemical ($C_1$-M-$C_2$) system according to any of embodiments described herein; and exposing the system to a stimulus, wherein the microstructure moves from a first relaxed position in which the functionalized portion is in contact with the first layer to a second actuated position in which the functionalized portion is in contact with the second layer, wherein the functionalized portion undergoes a chemical reaction with at least one component of one of the first and second layers.

In one or more embodiments, the system is capable of reversibly actuating and triggering the chemical reaction C2 in response to an external stimulus.

In one or more embodiments, the system is capable of reversibly actuating and triggering the chemical reaction C2 in response to the stimulus, which is a part of a feedback loop.

In one or more embodiments, the intended application is maintaining the temperature within a preselected range.

In another aspect, the chemo-mechano-chemical ($C_1$-M-$C_2$) system is used as a thermostat device that maintains the temperature in a narrow range for biomedical applications.

In one or more embodiments, the thermostat device maintains the temperature in a narrow range for an application in adaptive windows and insoles.

In another aspect, the chemo-mechano-chemical ($C_1$-M-$C_2$) system is used as microfluidic device that is used for sensing a variety of analytes.

In another aspect, the chemo-mechano-chemical ($C_1$-M-$C_2$) system is used as a microfluidic device that is used for sorting a variety of analytes.

In one or more embodiments, the analytes are chosen from the following non-exhaustive list: aptamer, protein, pathogen, antibody, biomolecule, organic molecule, inorganic molecule or ion, or cell.

BRIEF DESCRIPTION OF THE DRAWINGS

The invention is described with reference to the following figures, which are presented for the purpose of illustration only and are not intended to be limiting of the invention.

FIG. 7 is a photomicrograph of a top view of a microstructure surface (A) before and (B) after applying a catalyst, and (C) shows the tip functionalization by immobilizing fluorescent dye on the top surface of the microposts, visualized by fluorescence.

FIG. 12 is a photomicrograph of the chemo-mechano-chemical ($C_1$-M-$C_2$) system according to one or more embodiments used to activate the biochemical reaction of luciferin oxidation in the (A) OFF and (B) ON states illustrating the illumination of the treated microstructure tips when exposed to the appropriate reactants.

FIG. 13 is a plot of intensity vs. time to show the bioluminescence intensity as a function of time in an exemplary experimental system.

DETAILED DESCRIPTION

Self-Modulated Adaptively Reconfigurable Tunable Surface ('SMARTS') can interact with environmental cues in an adaptive, reconfigurable manner by the hydrogel-mediated movement of microstructures through a biphasic system, realizing the continuous interconversion of chemical and mechanical energy circuits. In response to a large variety of external stimuli such as pH, temperature, humidity, light, etc., the charge density or configurational nature of the polymer chains in the hydrogel changes, influencing its hydrophilic/hydrophobic nature. This results in a change in the osmotic pressure of the surrounding water solution as it surges into or flows out of the hydrogel, causing it to swell or contract. As the hydrogel swells, the volume change induces a force that causes microstructures that are embedded in the hydrogel to stand upright; conversely, as the hydrogel contracts, the microstructures are induced to bend. Such a mechanical reconfiguration of the microstructures induced by chemical changes in the gel represents a chemo-mechanical (C-M) process. This reversible chemomechanical C-M process can be extended to provide a Chemo-Mechano-Chemical ($C_1$-M-$C_2$) or a self-regulating autonomous C⇌M processes in which a chemically induced actuation of the microstructures triggers another chemical reaction, which itself may produce energy, induce propulsion, and/or create stimulus that brings about additional rounds of actuation. In such a self-regulating system the properties of the chemical reactions involved drive the system between different configurations.

By embedding catalyst-bearing 'skeletal' microstructures into a responsive hydrogel 'muscle' and introducing a fluid containing reactive 'nutrients', the platform allows precise control over a number of $C_1$→M→$C_2$ systems externally regulated by an applied stimulus. For example, if a pH- or thermo-responsive gels are used, one can tune various chemical reactions occurring in the reactant layer by changing external temperature or pH of the solution, such that induced chemical reactions of any kind (including inorganic, organic, biochemical) can be made to switch on and off with externally regulated frequency. Incorporation of carefully designed feedback mechanisms (C⇌M) into these systems has enabled continuous chemical, thermal and mechanical energy interconversions, resulting in autonomous, self-sustained materials, for example smart thermostats and structural materials that can autonomously self-regulate and maintain their temperature in a user-defined temperature range. A broad choice of chemical reactions, including biochemical reactions, if integrated with the highly tunable and customizable SMARTS, would open the doors to the control of innumerable sophisticated, environmentally friendly processes, including enzymatic or other biological activities.

Figure 1:
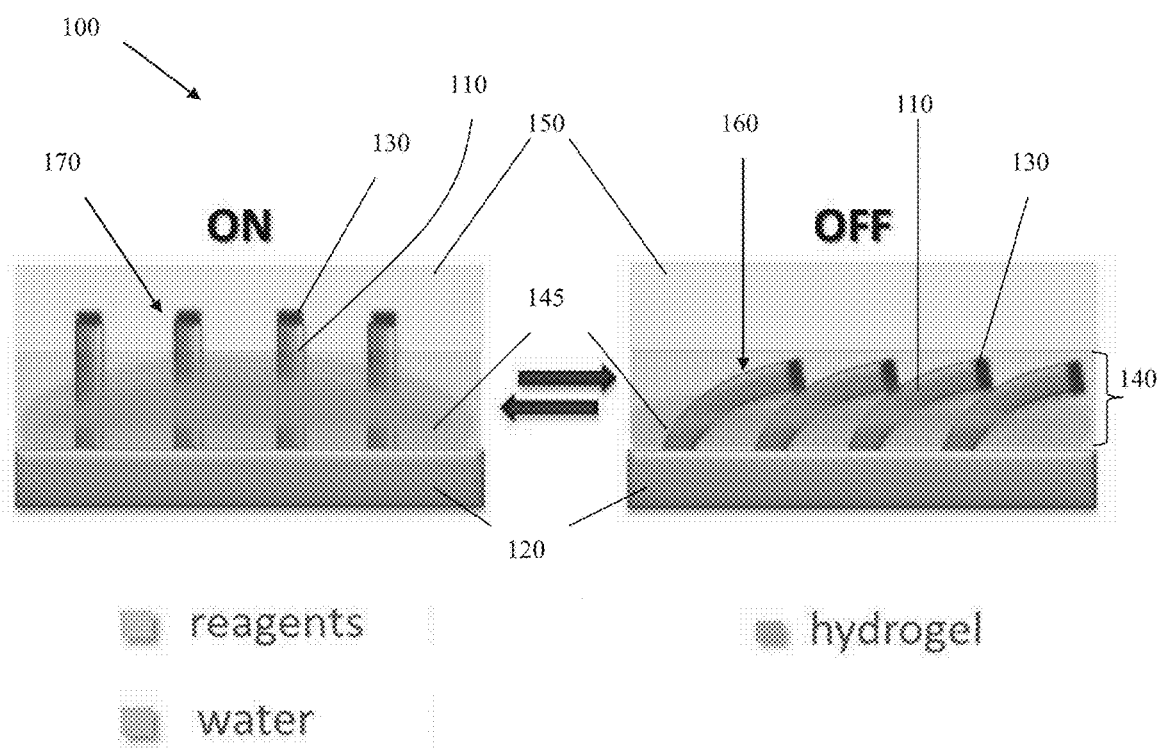
FIG. 1 is a schematic representation of a chemo-mechano-chemical ($C_1$-M-$C_2$) system according to one or more embodiments.

An exemplary self-regulating $C_1$-M-$C_2$ system is illustrated in FIG. 1. The microstructure features 100 (also referred herein as "SMARTS") made up of arrays of the "skeletal" high-aspect-ratio microstructures 110 on a base 120. The microstructures can be made of any materials; and generally they may or may not be attached to the base. For example, the microstructures can just be embedded in the gel without connection to the base. See, e.g., "Hydrogel-Actuated Integrated Responsive Systems (HAIRS): Moving towards Adaptive Materials", P. Kim, L. D. Zarzar, X. He, A. Grinthal, J. Aizenberg, Curr. Opin. Solid State Mater. Sci., 2011, 15 236-245, which is incorporated in its entirety by reference. Microstructures 110 are decorated at tips 130 with a reagent or catalyst that is involved in or facilitates a chemical reaction or other transformation. The microstructures are immersed in a liquid bilayer that is either immiscible or that does not mix significantly under system conditions. The lower layer 140 of the bilayer is the gel layer and includes a gel 145. Typically, gel 145 is a hydrogel and layer 140 is water; however, lyogels, oleogels or organogels (gels that swell in organic solvents) can also be used. Upper layer 150 is the reaction layer and contains reagents for a desired chemical reaction. The term 'chemical reaction' is used broadly to mean any transformation, such as chemical reaction, biochemical reaction or process, chemical or physical binding, adsorption, interaction or other modifications.

In operation, the hydrogel is capable of reversibly expanding and contracting and acts as a "muscle" on the microstructures. The action of the hydrogel on the microstructures provides the mechanical force ("M") in the $C_1$-M-$C_2$ system. In the "off" state, the hydrogel is in a first resting state and exerts a force on the microstructures that causes them to bend, as is shown at 160. The microstructures are below the interface with the upper layer and no chemical interaction takes place. A responsive volume change of the hydrogel is induced in the hydrogel by a stimulus applied to the bottom liquid layer, $C_1$. The stimulus causes the hydrogel to undergo a volume change and to transition into the second, "on" resting state, which exerts a force on the embedded microstructures and reversibly drives their actuation ($C_1 \rightarrow M$). Upon actuation, the functionalized tips 130 move into the upper liquid layer 150, causing the functionalized tips 130 to interact with the reagents in the upper liquid layer 150, as shown at 170. The functionalized tips 130 mediate a chemical interaction with the reagents in upper liquid layer 150 ($C_2$). As discussed in detail below, the chemical reaction may additionally involve generation of light, gas and heat, etc. In this fashion, the responsive actuation itself, ($C_1 \rightarrow M$) provides a means to turn "on" or "off" chemical reactions ($C_2$) taking place in the upper layer of the liquid system ($C_1 \rightarrow M \rightarrow C_2$). If $C_2$ in fact is the same as, or can trigger $C_1$ (e.g., the chemical reaction $C_2$ is exothermic and the hydrogel is temperature responsive), then this unique system provides a means for a chemomechanical feedback loop ($C \leftrightarrows M$).

The system can be arranged so that the chemical reaction takes place in the lower hydrogel-containing region. In this case, when the reaction is taking place in the bottom layer with the bent structures, the reaction is OFF when they straighten, and they can straighten into the upper layer that can be a liquid or even gas, such as nitrogen, air, or any other suitable gas or mixture, without a need for a liquid upper layer, as illustrated in FIG. 27.

Figures 24A, 24B:
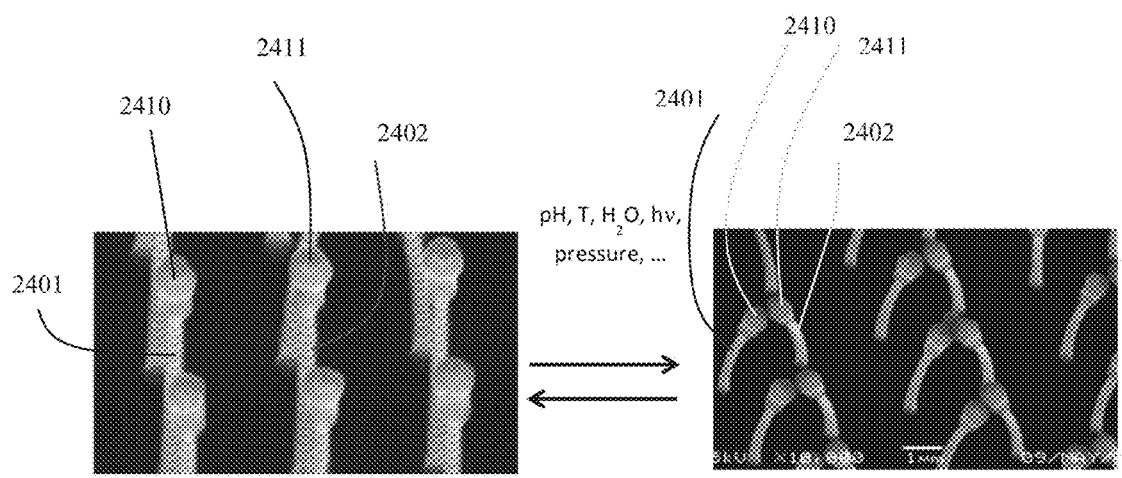
FIGS. 24A and 24B show images of tip-decrated microstructures standing upright, not in contact with each other (24A) and coming in contact pairwise (24B), illustrating how a chemo-mechano-chemical ($C_1$-M-$C_2$) system can be initiated upon contact of one or more microstructure tips according to one or more embodiments.

The chemical reaction may also be initiated in other modes. For example, the microstructure tips may be functionalized with different reagents that are not reactive until contacted with one another, as illustrated in FIGS. 24A and 24B. Upon activation, neighboring microstructure tips 2401, 2402 move from a first spaced apart position (FIG. 24A) to a second contacting position as shown in FIG. 24B. The posts are decorated with chemical reagents 2410, 2411 at their tips. When the gel contracts, the tips of the posts touch, bringing reagents 2410 and 2411 together, and may initiate a chemical reaction (FIG. 24B). A person skilled in the arts of micro- and nanofabrication and lithography can deduce a number of approaches that would force the spatial bias onto the microstructure arrays or onto the responsive gel that would result in the type of arrayed pair-wise bending of the microstructures. These approaches include, but are not limited to using appropriately-designed masks during photocuring steps, as wells as a variety of gel patterning techniques. In one embodiment, the underlying gel is patterned into stripes of varying thickness and width corresponding to double distance between the microstructures, the row of microstructures embedded in a stripe where the gel bulges will bend toward each other and touch. Patterning techniques used to generate such 'patterned touching' is described in "Hydrogel-Actuated Integrated Responsive Systems (HAIRS): Moving towards Adaptive Materials", P. Kim, L. D. Zarzar, X. He, A. Grinthal, J. Aizenberg, Curr. Opin. Solid State Mater. Sci., 2011, 15 236-245, which is incorporated in its entirety by reference. The appropriate selection of reagents and/or catalysts may result in an exothermic reaction, or a bioreaction or other reaction to occur.

Figure 25A:
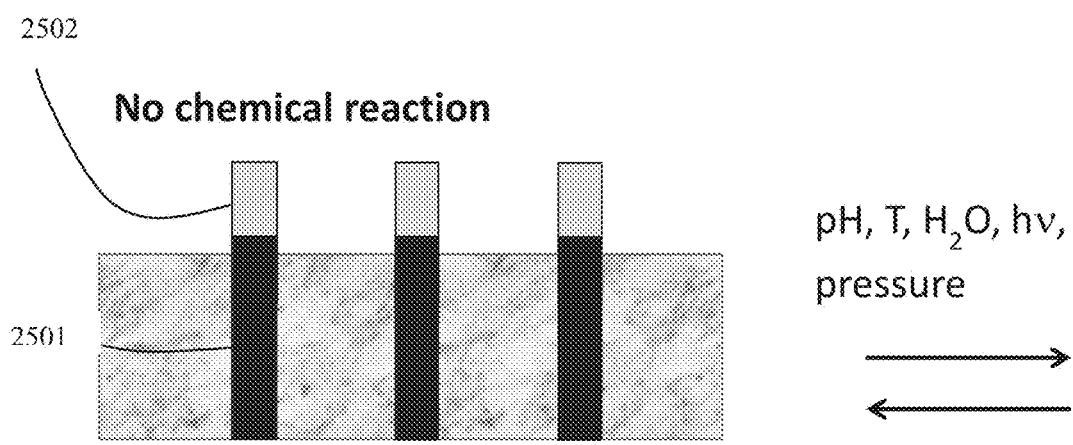
FIGS. 25A and 25B are schematic illustrations of a chemo-mechano-chemical ($C_1$-M-$C_2$) system in which a microstructure is locally decorated with two reactants that come in contact and interact upon microstructure bending according to one or more embodiments.
Figure 25B:
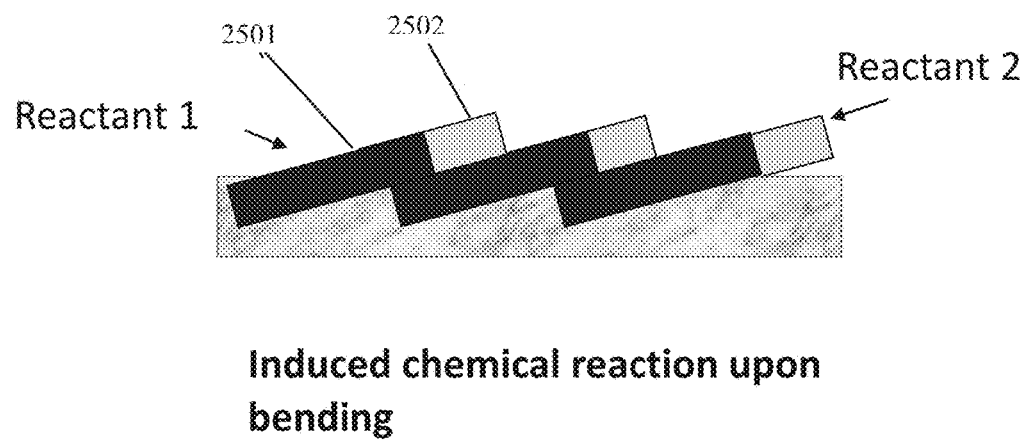

In other embodiments, the outer surface or wall 2501 of the microstructures may be functionalized, embedded or decorated with different reagents that are not reactive until contacted with the reactant 2502 deposited on the top part of the microstructures, as shown in FIG. 25A. Upon bending, the top reactant 2502 comes in contact with the bottom reactant 2501 and initiates a chemical reaction, as shown in FIG. 25B. Bending can be initiated by a volume change of a hydrogel surrounding the base of the microstructures. Initiation can be triggered by any conventional method, for example, pH, T, $H_2O$, ultraviolet or other light irradiation, pressure.

Figures 27A, 27B:
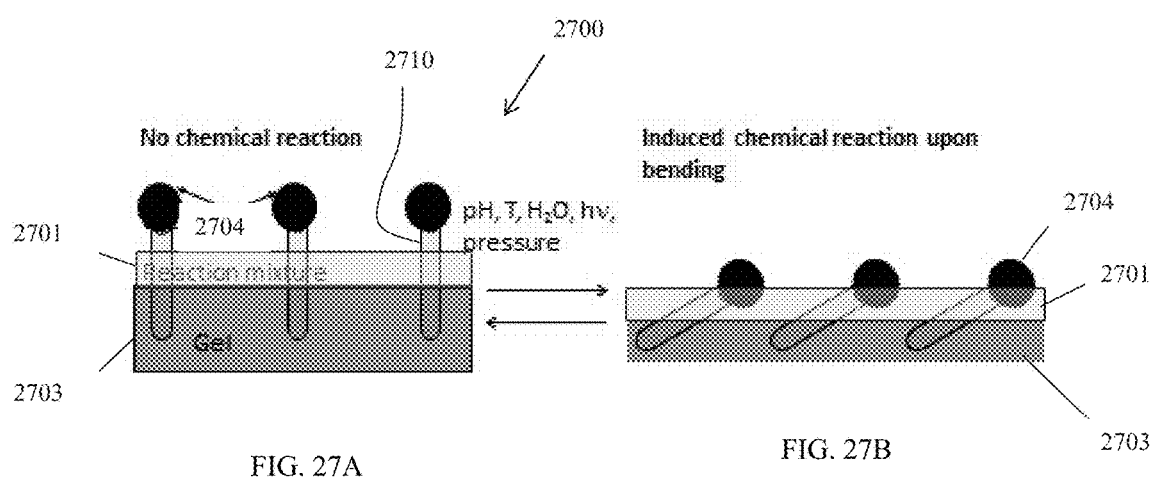
FIGS. 27A and 27B are schematic illustrations of a chemo-mechano-chemical ($C_1$-M-$C_2$) system in which the catalyst for chemical reaction is located above the reactant mixture, when the gel is in an expanded state and the microstructures are in the upright position, and the $C_2$ reaction is switched ON upon bending of the catalyst-encrusted pillars and OFF upon gel swelling as a result of the chemical reaction, according to one or more embodiments.

In other embodiments, the reactants are in the bottom layer and the reaction is induced upon bending rather than expansion. As illustrated in FIG. 27A, a SMARTS system 2700 can include microstructures 2710, an upper reaction layer 2701 and a lower hydrogel layer 2703. The tips 2704 of the microstructures are decorated, for example, with a catalyst and extend above the reaction layer. Thus, no reaction takes place in the inactivated state. Upon activation, hydrogel in the hydrogel layer contracts and the microstructures are bent so that the catalyst tips now contact the reactive layer and a chemical reaction ensues, as is illustrated in FIG. 27B. As noted above, a self-regulatory homeostatic system can be developed when the reaction produces a signal that triggers the swelling of the hydrogel.

The exemplary method for creating the platform for such a device includes the production of replicas, e.g., polymer replicas, of a periodic array of high-aspect-ratio "master" structures. A negative replica of the "master" silicon microstructures is fabricated, for example with polydimethylsiloxane (PDMS), and this mold is subsequently filled with a desired precursor solution, including, but not limited to epoxy solution, which is then cured/solidified to produce a replica of the original "master" microstructures in the material of choice. The choice of master microstructures and materials for making them is quite broad. It can be an array of high-aspect-ratio structures of any origin, for example, carbon nanotubes, silicon, even including biological samples that can be replicated or used directly (with appropriate tip decoration and positioning into gel and a bilayer system. A non-limiting review of such double replication methodology is presented in P. Kim, L. D. Zarzar, X. Zhao, A. Sidorenko, J. Aizenberg. "Microbristle in gels: Toward all-polymer reconfigurable hybrid surfaces." Soft Matter, 2010, 6, 750-755, and Hydrogel-Actuated Integrated Responsive Systems (HAIRS): Moving towards Adaptive Materials", P. Kim, L. D. Zarzar, X. He, A. Grinthal, J. Aizenberg, *Curr. Opin. Solid State Mater. Sci.*, 2011, 15 236-245, which are hereby incorporated by reference in its entirety. The microstructure "skeletal" platform is then infused with and linked to a hydrogel that has reversible swollen and contracted states. A hydrogel solution can be applied around the base of the microstructures. The swelling and contraction of the polymeric hydrogel leads to actuation of the microstructures.

Figures 2A, 2B:
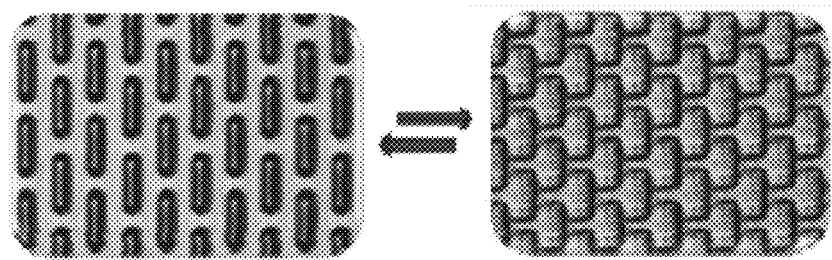
FIGS. 2A and 2B are photomicrographs of an exemplary experimental system, providing a top view of blade-shaped microstructures that can undergo reversible movement between (A) an upright (ON) state and (B) a bent (OFF) state.

FIGS. 2A and 2B are photomicrographs of blade-shaped microstructures as they undergo reversible movement between an upright (ON) state and a bent (OFF) state. In FIG. 2A, blade-shaped microstructures are shown as viewed from above. The blades are upright and the blade tips project into the upper liquid layer 150. This image corresponds with the ON state of FIG. 1. In FIG. 2B, the blades are bent to one side so that they are deflected down into the lower water layer 140 of the liquid bilayer. This image corresponds with the OFF state of FIG. 1.

The microstructures can take on a range of shapes and dimensions. In non-limiting embodiments, the microstructures are of uniform cross-section, e.g., bristles, rods, columns and the like. In other embodiments, the microstructures are anisotropic and have one cross-sectional dimension that is larger than the second, e.g., paddles, plates or fins. In yet other embodiments, the microstructures can have, within the same device, different aspect ratios, heights, and mechanical characteristics. Microfins that are 2 µm-thick, 10 µm-long and 18 µm-tall are mainly used in the demonstration here, and 10 µm-diameter, 100 µm-tall microposts are used in the SEM showing the morphology when embedded in hydrogel. The whole system can be scaled either down or up in its size, that is, the examples show 2-10 micron range in feature sizes, but it can be anything from submicron to millimeter range and likely even bigger. Anisotropic microstructures have the advantageous tendency to deflect in the same direction in response to the mechanical force imposed by the hydrogel expansion or contraction. It is also possible to introduce a bending preference into uniformly shaped structures by prestressing the structure during hydrogel formation or by introducing stress as the microstructure mold is removed from its casting. Preferential bending modes can also be introduced by curing the hydrogel so that the swelling and contraction response is non-uniform on either side of the microstructures.

The microstructures can be made from a range of materials. The material is selected for its chemical inertness to the chemical reactions used to provide the triggering reactions. In addition the microstructures can be made from materials that provide the desired mechanical properties of strength, flexibility, Young's Modulus, etc. that are desired for the mechanical movements of the system. Other material considerations in the selection of materials include mechanical robustness to multiple reversible mechanical bending cycles, satisfactorily low or high hysteresis, as preferred for the particular application, flexural modulus for the capability of bending/actuating, and conductive surface or body or both, if necessary. In one or more embodiments, the system can be reconfigured in a variety of other geometrical combinations taking into account the particular material and dimensions of microstructures and the desired arrangement/compositions of the immiscible liquid phases. In some embodiments, the microstructures can be distributed in an ordered or disordered manner on the surface.

Figure 3:
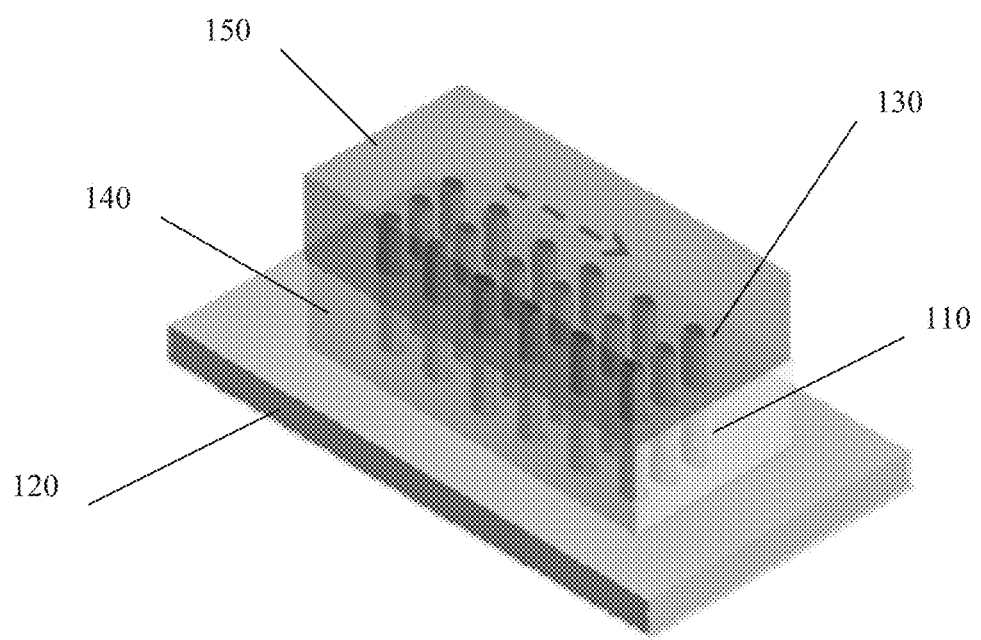
FIG. 3 is a perspective drawing of an exemplary chemo-mechano-chemical ($C_1$-M-$C_2$) system according to one or more embodiments.

The biphasic system can be used in both static systems and dynamic flow systems, increasing the capabilities of the device. One exemplary configuration is illustrated in FIG. 3, in which previously identified elements are similarly labeled. The bilayer can be made of immiscible liquids so that there is little or no mixing between the two layers. In some embodiments, a static interface may increase the effectiveness of the feedback loop, for example, when the triggering event is temperature.

In one or more embodiments, a biphasic microfluidic design is contemplated. In one configuration of a dynamic biphasic system, the laminar flows of two fluid layers are introduced over the microstructures such that the tips of the microstructures when they are upright within a swollen hydrogel are exposed to the top fluid layer but are inaccessible to the top layer when the microstructures bend within a contracted hydrogel. In one or more embodiments, the bilayer is made of miscible liquids. For example, aqueous solution: aqueous-aqueous bilayer can be formed by laminar flow in microfluidic channel. Organic solution can also be used. If the organic solvent has a density lower than water, an organic-aqueous bilayer can be formed by itself due to self-phase-separation between organic liquid and water. If the organic solvent has a density higher than water, an organic-aqueous bilayer is also formed by itself but has inverted, upside down configuration, i.e., water as top layer and organic solution as bottom layer, in which case the hydrogel-embedded microstructures will be fabricated upside down too, on the top side of the device. In other embodiments, the phases may be arranged in a side-by-side configuration in which both the hydrogel layer and the second layer are positioned in the same plane. The microstructures can be embedded in the hydrogel layer and caused to go in and out of the second layer during C→M transitions.

Figure 4A:
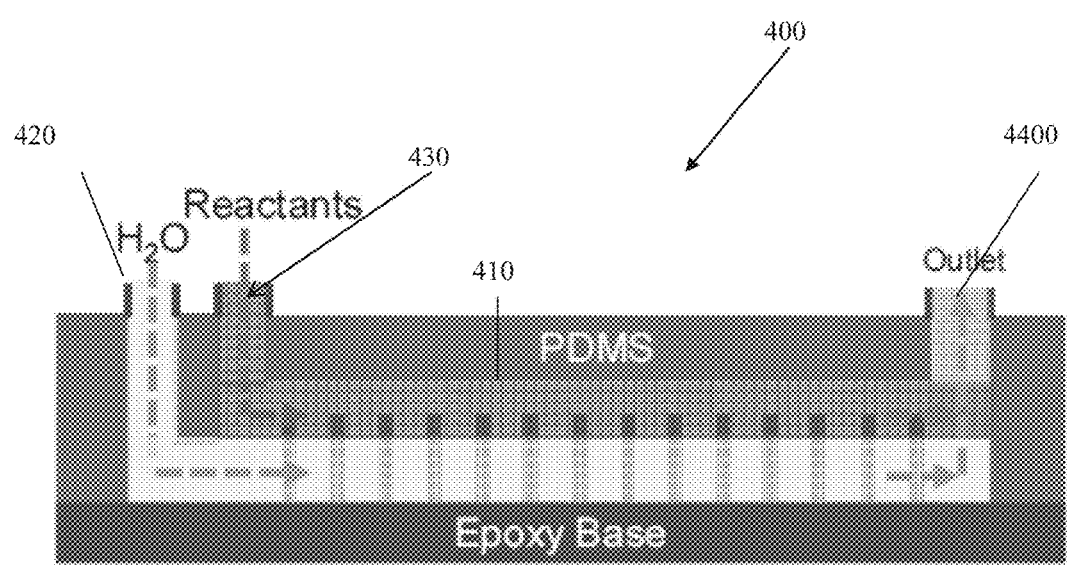
FIG. 4 is a (A) cross-sectional and (B) exploded view of a dynamic microfluidic chemo-mechano-chemical ($C_1$-M-$C_2$) system according to one or more embodiments.

An exemplary microfluidic system 400 is illustrated in FIG. 4A. The microfluidic device includes a channel 410 in which different liquids flow in laminar pathways through microstructures embedded in hydrogel as described above. A first inlet 420 feeds the gelling solvent, e.g., water, into a lower portion of channel 410, while a second inlet 430 feeds reagents into an upper portion of channel 410. The relative flow paths of the two layers minimize mixing. A common outlet 440 can be used for both liquid flows; however, separate outlets for the two fluid flows are contemplated, as well. See, e.g., FIG. 17b. The microfluidic system allows modification of inlet fluid composition so that the gel state of the hydrogel can be controlled. For example, if the hydrogel is pH sensitive, the gel state can be transitioned by changing the pH of the inlet fluids. In other embodiments, the microfluidic system is arranged to permit exposure to external stimuli, such as heat or light energy, to trigger the gel transition.

Figure 4B:
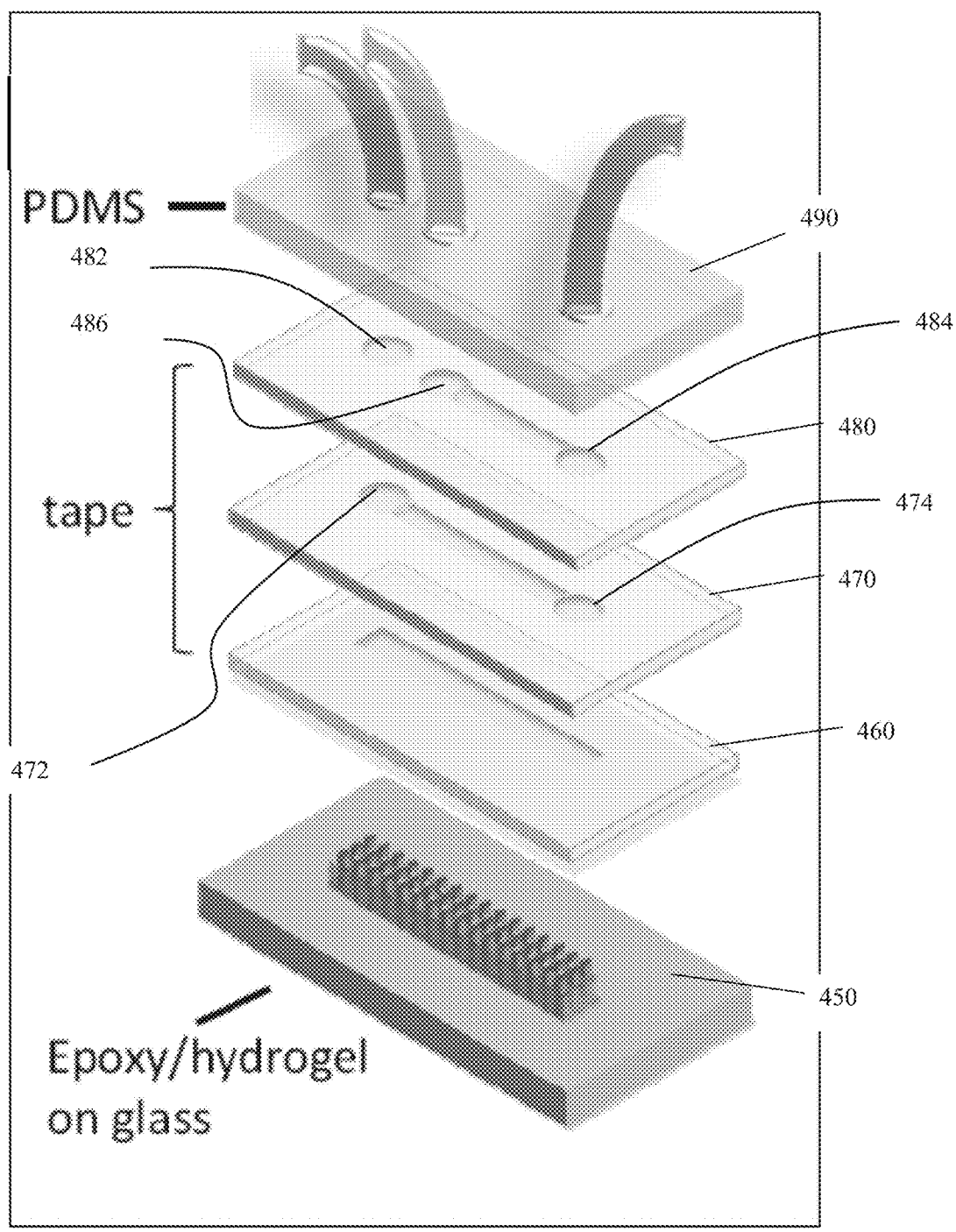

Assembly of an exemplary microfluidic device is shown in FIG. 4B in exploded view. An epoxy substrate 450 including base and microstructure is provided. The microstructures are raised above the base and occupy the channel of the microfluidic device. Layers of tape with certain thickness and cut according to the channel dimensions are placed one on top of another to define the features, e.g., shape and height, of the channel. The height of microstructures located within the channel then determines the possible range of heights for the interface of the liquid bilayer in the microfluidic device, as discussed in greater detail below. Small inlets and outlets are cut into these tape layers. A first layer 460 includes a cut out to accommodate the microstructures. A second layer 470 is positioned above layer 460 and includes an aperture 472 for receiving fluid flow and directing it to a lower portion of the channel and an aperture 474 to direct fluid from the channel and into the outlet. A third tape layer 480 is positioned over layer 470 and includes a spaced apart aperture 482 in fluid communication with the aperture 472 in the lower layers as well as an aperture 486 for receiving the reagent fluids and directing them to an upper portion of the channel and an aperture 484 to direct fluid from the channel and into the outlet. A final sheet of a PDMS mold with the same inlets and outlet is placed on top. Fluids are then able to flow into these inlets through small tubes, which allow for biphasic laminar flow through the hydrogel-embedded microstructures.

Figure 5:
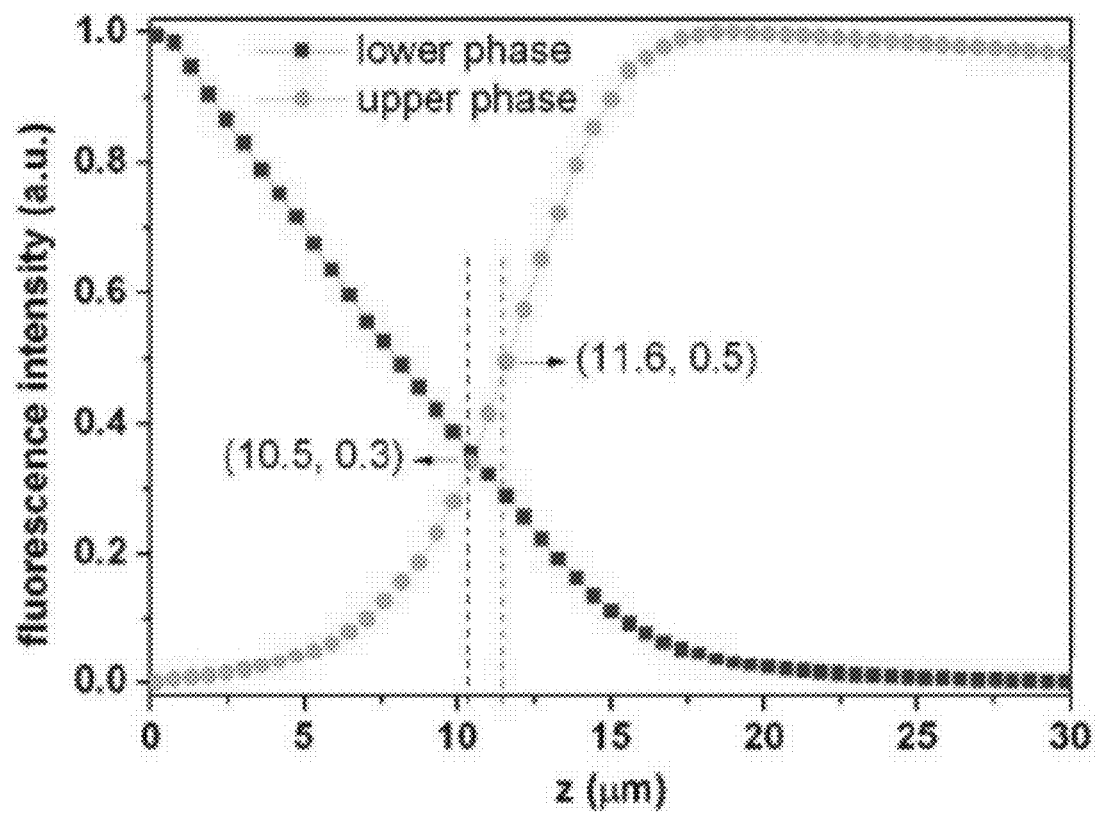
FIG. 5 is a plot of fluorescent intensity vs. height (z) illustrating the location of the interface between the two liquids of the bilayer in an exemplary experimental microfluidic chemo-mechano-chemical ($C_1$-M-$C_2$) system according to one or more embodiments.

By adjusting the relative flow rates of the reactant and water layers, it is possible to control the height at which the interface occurs. The interface desirably occurs at such a height that the tips of the nano/microstructures are exposed to the top fluid layer when upright and, in contrast, exposed only to the bottom fluid layer when bent. By adjusting the height of the microfluidic channel 460 and the flow rates of the two liquids, a range of interface locations are achieved. In one non-limiting embodiment, for a microfluidic channel having a height of about 120 μm, the interface can be located between about 10 μm and about 60 μm. In yet another embodiment, for a microfluidic channel having a height of about 180 μm, the interface can be located between about 35 μm and about 90 μm. In non-limiting embodiments, the bilayer interface is set at around half to two thirds the height of the microstructures. For example, the bilayer interface is targeted for about 12 μm for the 18 μm-tall micro-fin. FIG. 5 is a plot of fluorescent intensity vs. height (z) illustrating the location of the interface between the two liquids of the bilayer in a microfluidic chemo-mechano-chemical ($C_1$-M-$C_2$) system containing two different fluorescent dyes according to one or more embodiments. The intersection of the measured fluorescence intensity of the top fluid layer (containing a fluorescein solution) and bottom fluid layer (containing a rhodamine B solution) indicates the height of the interface of the two liquid layers.

Figure 6:
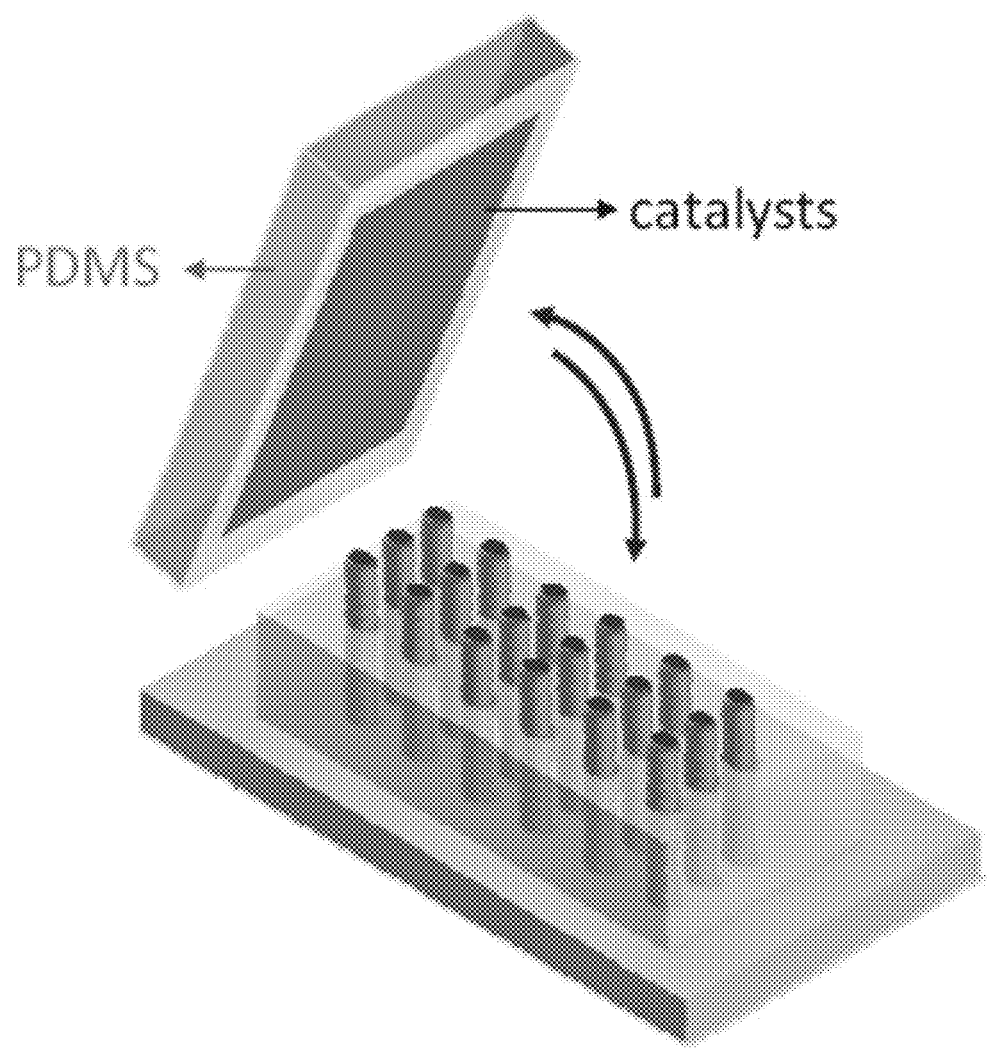
FIG. 6 is a perspective illustration of a stamping process for applying a catalyst or reagent to the system according to one or more embodiments.

Localization of catalysts or reagents onto the tips of the microstructures can be carried out by known techniques, including chemical covalent attachment, by physical adsorption, metal electrochemical deposition, sputter-coating, chemical vapor deposition, stamping, screen printing and the like. A non-limiting description of a number of methods for depositing materials on the tips of the microstructures are presented in "Fluidics-Induced Localized Assembly of Materials Using a Superhydrophobic Surface Structure", J. Aizenberg, B. Hatton, U.S. patent application Ser. No. 12/745,207, filed May 27, 2010, which is incorporated here as a reference in its entirety. In one embodiment, functionalization of the microstructure tips was carried out by PDMS stamping method, as shown in FIG. 6, followed by thorough rinsing with water or corresponding solvent to remove excessive unbounded catalysts. The SEM images in FIGS. 7A and 7B show the morphology of hydrogel-embedded 100 μm-tall microposts with the top 20 μm sticking out of the gel. The tip functionalization is demonstrated by immobilizing fluorescent dye on the top surface of the microposts. The selective modification of the microstructures, visualized by fluorescence microscopy (FIG. 7C), enables the precise control of the occurrence and ceasing/termination of the reaction on the top layer of the SMART system.

The chemo-mechano-chemical ($C_1$-M-$C_2$) system is versatile and can employ a range of stimuli to activate the hydrogel. The hydrogel used in the chemo-mechano-chemical ($C_1$-M-$C_2$) system can be selected to exhibit a responsive volume change under a range of conditions. Hydrogels are known for example to undergo reversible volume change over a range of temperatures and a range of pH or ionic strength values. Selection of a suitable hydrogel can be accomplished using known hydrogels or by modifying hydrogels according to known methods. See, e.g., Okano, T., Bae, Y. H., Jacobs, H., & Kim, S. W. Thermally on-off switching polymers for drug permeation and release. *J. Controlled Rel.* 11, 255-265 (1990); and Philippova, O. E., Hourdet, D., Audebert, R., & Khokhlov, A. R. pH-Responsive Gels of Hydrophobically Modified Poly(acrylic acid). Macromolecules 30, 8278-8285 (1997); Mark A. Ward and Theoni K. Georgiou, Thermoresponsive Polymers for Biomedical Applications, *Polymers,* 2011 (3) 1215-1242, which are incorporated herein by reference.

Furthermore, hydrogels responsive to a variety of other external cues including a magnetic field, an electric field, light, electron transfer, etc, can be employed, giving the $C_1$-M-$C_2$ system great versatility. Further examples of suitable gels include multi-responsive gels that are sensitive to pH, temperature, light, and mechano-sensitive hydrogel, gel networks, including interpenetrating networks of two polymer networks which are bound together by physical entanglement, such as polyacrylic acid (PAA) and polyacrylamide (PAAm), PNIPAAm-co-PAAc, etc., and organogels (while hydrogel needs to be immersed in water or aqueous solution in order to change its volume phase, i.e. swell and contract, organogels swell and contract in organic solution as the medium, which allows for larger variety of device designs, especially where organic solution needs to be the bottom layer), for broader applications. Examples of stimuli-responsive gels are not meant to be exhaustive and those skilled in the art should be able to understand that a wide variety of polymer and gel systems, including interpenetrating, semi-interpenetrating networks, double networks, etc. can be used for any stimulus-responsive action.

In one or more embodiments, the responsiveness of the hydrogel to pH or temperature is optimized, developing a system that is suited to the particular chemical reaction of interest, e.g., chemical/biological reactions. Polymeric hydrogels are composed of cross-linked polymer networks, responsive to different stimuli, polymerized under, e.g., the application of UV light. In one or more embodiments, temperature- and pH-sensitive hydrogels are used, although response to other stimuli can be easily incorporated into the device. Hydrogels responsive to pH are composed of ionizable groups which are a weak acid or base such that the hydrogel can be induced to swell or contract in an acidic or basic environment. An exemplary pH-responsive hydrogel is composed of anionic cross-linked acrylic acid (AAc) and acrylamide in a copolymer network. The transition pH above which the hydrogel swells according to the degree of ionization in the hydrogel network is determined by the pKa of AAc, which is typically about 4.25. At pH>pKa, AAc the AAc is ionized, which leaves the hydrogel polymer network with a net charge. This increases the hydrophilicity of the hydrogel, and water infiltrates the network leading to swelling. At pH<pKa, AAc the AAc is non-ionized and neutral, so the hydrogel polymer chains become more hydrophobic and water is expelled, causing contraction. Various other formulations of the pH-responsive hydrogel are possible. An exemplary temperature-responsive hydrogel is composed of N-isopropylacrylamide, NIPAAM, cross-linked with bis-acrylamide. See, e.g., Schild, H. G. Poly(N-isopropylacrylamide): experiment, theory and application. *Prog. Polym. Sci.* 17, 163-249 (1992), which is incorporated herein by reference. At low temperatures, the gel is in its extended, hydrophilic (swollen) state and it undergoes a sharp volume decrease at the transition temperature or lower critical solution temperature (LCST), which is typically about 32° C. Above this temperature, the gel is in its contracted, hydrophobic (shrunken) state. By altering the ratio of certain monomers or by introducing comonomers bearing alkyl substituents into the mixed monomer pre-gel solution, it is possible to tune the responsiveness of the hydrogel to the pH or temperature as desired. Various other formulations of the temperature-responsive hydrogel are possible. For instance, regarding biological enzymatic reactions such as the bioluminescence reaction in which the enzyme luciferase is used, the transition pH, or the pH above which the hydrogel swells, can be altered to a pH at which the enzymes remain active. For example, the transition pH of the AAc hydrogel was altered from 4.3 to a transition pH of around 7.0 by introducing a comonomer bearing a lengthy alkyl substituent into the precursor pH-responsive hydrogel solution to produce a pH-sensitive hydrogel at a physiological pH. Similarly, it is possible to decrease the transition temperature of the thermoresponsive hydrogel by the incorporation of butyl methacrylate, BMA. In this way one can tune or "program" the responsiveness, and thus increase the usefulness of the device with regard to the particular chemical/biological system of interest.

"Smart" adaptively reconfigurable devices that interact with biomolecules in response to stimuli provide a unique solution for biomolecule detection, separation, purification and concentration of complex mixtures or biofluids including, but not limited to, blood and serum.

The chemo-mechano-chemical ($C_1$-M-$C_2$) system can also be designed for a wide range and type of chemical reactions in the upper layer of the bilayer system. By way of example, the chemical reaction occurring in the upper layer can include biochemical reactions, such as enzymatic reactions (see FIG. 11) or specific or nonspecific biomolecule binding reactions (see FIG. 17-19), organic reactions (see FIG. 9, 10, 21, 22), inorganic chemical reactions, such as gas generation (see FIG. 16), or physical interactions, such as fluorescence quenching (see FIG. 14).

The hydrogel, microstructures and catalyst can be selected and varied to provide a number of different actuation characteristics. For example, the system can be designed so that specific regions of the device actuate under different conditions or times. In additions, the catalyst decorating the tips of the microstructures can be varied so that different reactions are catalyzed. In other embodiments, microstructures of different heights, thicknesses and materials can be used to provide different actuation responses.

Autonomous, Self-Regulated Systems that Maintain Constant T

Of particular interest is the ability to design self-regulated, autonomous $C_1 \rightarrow M \rightarrow C_2$ systems in which the chemical output signal is matched with the stimulus of the responsive hydrogel. Such a system shows homeostatic behavior due to the continuous feedback loop, $C \rightarrow M \rightarrow C \rightarrow M \rightarrow \ldots$ or $C \leftrightarrows M$. Several exemplary self-powered, self-regulated oscillating systems are provided that use coupling the mechanical action of a temperature-responsive gel, poly(N-isopropylacrylamide) (pNIPAAm) with a temperature generation occurring in the switched exothermic reaction that takes place in the top layer. Such systems are presented for the purpose of illustration only; it is contemplated that a range of systems employing a variety of chemistries, gels and triggering conditions can be employed. Exemplary systems with several exemplary exothermic catalytic reactions include:

(i) hydrosilylation of 1-hexene with triethylsilane catalyzed by $H_2PtCl_6$

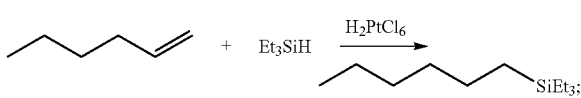

(ii) hydrosilylation of 1-hexene with diphenylsilane catalyzed by $H_2PtCl_6$

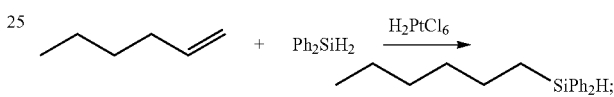

(iii) decomposition of cumene hydroperoxide catalyzed by $Ph_3CPF_6$

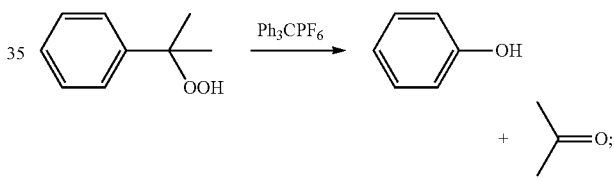

(iv) "click" reaction between octylazide and phenylacetylene catalyzed by $Cu(PPh_3)_2NO_3$

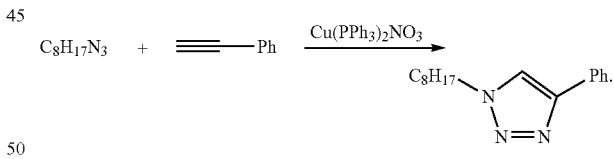

Figure 23:
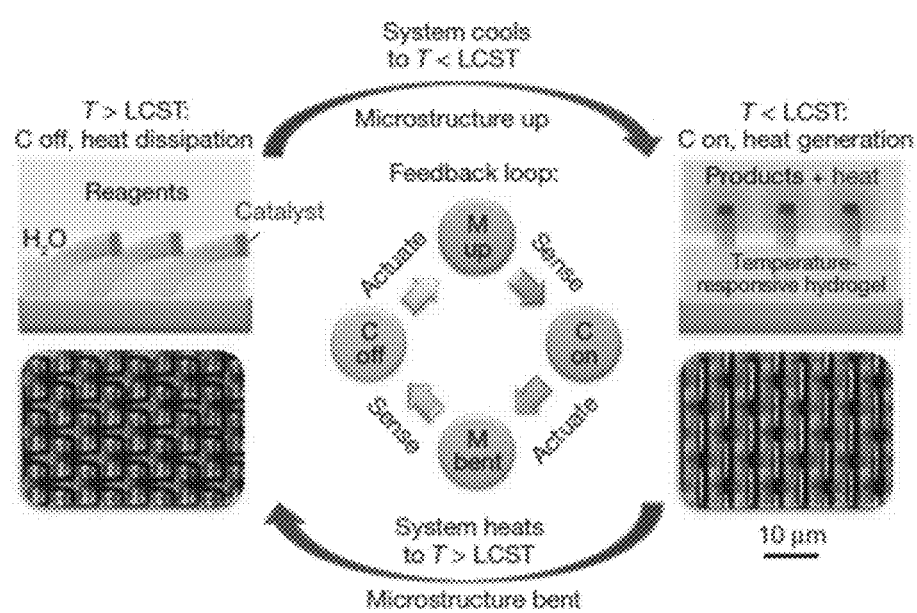
FIG. 23 shows a schematic of the conceptual design of temperature-regulating, autonomous, homeostatic SMARTS showing a C M feedback loop, in which mechanical action of temperature-responsive gel is coupled with an exothermic reaction; the side-view schematic and top-view microscope images depict on/off states of the reaction in the top layer.

Below the lower critical solution temperature (LCST), the thermally-responsive hydrogel swells, the embedded microstructures straighten, and their catalyst-functionalized tips enter the reagent layer, triggering an exothermic reaction. When the temperature increases to T>LCST due to the generated heat, it triggers contraction of the hydrogel, removing the microstructures from the reagents. When the temperature falls to T<LCST again, the cycle restarts, giving rise to continuous, self-regulated $C \leftrightarrows M$ oscillations. This self-regulating cycle is illustrated in FIG. 23. All these systems behave as autonomous thermal regulators that, within a very narrow range, maintain a local temperature, which is largely determined by the LCST of the hydrogel.

The ability of SMARTS to maintain a stable temperature can be used in autonomous self-sustained thermostats with applications ranging from medical implants that help stabilize bodily functions to 'smart' buildings that regulate thermal flow for increased energy efficiency. The thermostat can operate under conditions where batteries and electric circuits are undesirable or must be avoided.

Switchable Biochemical Reactions

Figure 11:
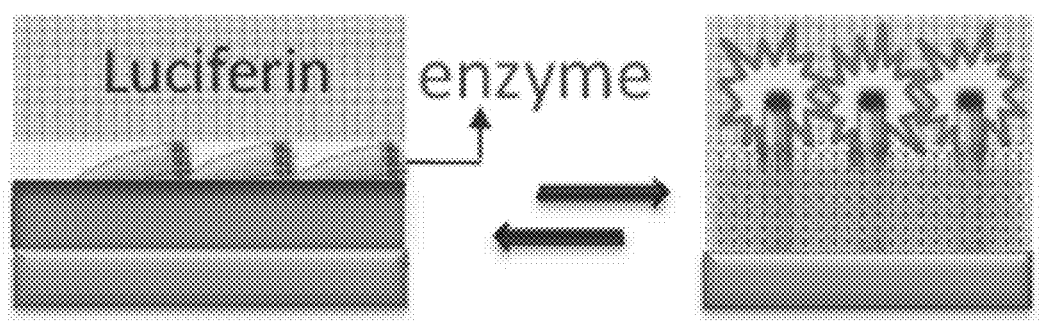
FIG. 11 is a schematic illustration of a chemo-mechano-chemical ($C_1$-M-$C_2$) system according to one or more embodiments used to activate the biochemical enzymatic reaction of luciferin oxidation.

The exquisite controllability provided by SMARTS, which enables the transport of biomolecules between distinct aqueous environments via the microstructure actuation, allows externally regulated, switchable biochemical reactions with programmable cycles and outputs. For example, chemo-mechanically mediated cyclic "on-off" switching of an exemplary enzymatic reactions, such as the luciferase (LUC)-catalyzed oxidation of luciferin, is possible using SMARTS (FIGS. 11-13). In this system, pH changes are converted to mechanical movement, which in turn triggers a biochemical reaction that generates light. In this way, a signal cascade/converter capable of translating signals at the nano-scale to outputs that can be visualized at the macro-scale is possible.

The precise and swift on/off switching of the bioluminescent reaction across the bi-liquid interface demonstrates the excellent coordination of the chemically-induced mechanical motion ($C_1 \rightarrow M$) with the mechanically-modulated enzymatic activity ($M \rightarrow C_2$). Using periodic changes in pH in the bottom layer as the stimulus, a synchronous cascade of chemo-mechano-(bio)chemical light generation cycles is realized. Through pH-mediated swelling of the hydrogel "muscle", the coordinated bending of tens of thousands of catalyst-decorated microstructures generated light in the top fluid layer that was visible to the naked eye. This type of multi-scale cascade provides readouts of unrelated but coupled chemical events (i.e., pH change to light emission), and can be used to arbitrarily couple a vast range of reactions.

In summary, precise control of biochemical signal transduction is demonstrated using the model system of luciferease bound to micro-structure tips that catalyzes the oxidation of luciferin in a periodic, switchable fashion. The SMARTS device is shown to be both compatible with delicate biological constraints and capable of accommodating enzymatic reactions for signal transduction, attributed to its modularity, tunability, and physical simplicity. Moreover, the hybrid hydrogel-microstructured surface is well integrated in a microfluidic channel, showing that this chemo-mechanical system can be readily applied in microfluidic lab-on-a-chip systems to create effective, complex, and highly integrated microfluidic networks for biological automation. The potential variety of switchable biochemical reactions that could be accommodated by this $C_1 \rightarrow M \rightarrow C_2$ cascade is complemented by the customizability of the hydrogel response, which can, in turn, be tailored to a wide range of stimuli, such as pH, heat, light, glucose or other metabolic compounds. The use of biological macromolecules in SMARTS can enable vast varieties of outputs, such as gas generation (e.g. catalase decomposition of $H_2O_2$), color change (horseradish peroxidase-catalyzed oxidization of resorufin), DNA polymerization, and proteolysis to name only a few, thus improving the combinatorial diversity of coupled effects.

In other embodiments, the oscillating system can be used for signal amplification. Short DNA tags can be bound to the microfin tips, and can be used to generate long, repetitive DNA strands for specified amounts of time. These strands can be all be tethered at the same end, and can have long, repetitive ssDNA sequences dangling from the structure tips. By actuating the microstructures, the tips are immersed into the upper fluid layer, which contains circular DNA templates, dNTPs and DNA polymerase. During this immersion phase, the DNA continues to grow, but remains tethered to the substrate. When the plates are returned to their lower position, the strand growth ceases, but the DNA strands remain attached. Depending on downstream applications, this method allows for generation of repetitive aptamer sequences for signal amplification, or even switching of DNA sequence on the same strand by changing the circular DNA template between actuations.

Selective Capture and Release of Biomolecules

While many other sorting/sensing systems modify their target molecule irreversibly, the high affinity handle of nucleic acid incorporated into SMARTS allows one to sort biomolecules without modification. While any binding molecule, and in particular those that bind with specificity, can be used with SMARTS, nucleic acid aptamers present an attractive alternative to antibodies for several compelling reasons: (1) aptamers typically have high affinities (nano-molar to picomolar) for their protein targets, and are capable of binding these targets with high selectivity, due to the SELEX selection process which can incorporate negative selection against off-target proteins; (2) aptamers are stable in more extreme pH and temperature conditions than antibodies, which require physiological conditions; (3) solid-phase DNA synthesis enables rapid, reproducible production of chemically modified aptamers; and (4) using SELEX, aptamers can be raised against almost any target of interest, including small molecules, proteins, and whole cells. Importantly, unlike antibodies, aptamers can be reversibly denatured and refolded in response to temperature or pH changes, enabling repeated cycles of controlled capture and release in the stimuli-responsive microdevice.

The chemo-mechano-chemical ($C_1$-M-$C_2$) system is capable of both sensing and sorting. In one of the embodiments, detection of the analyte is made for sensing purposes. In other embodiments, specific binding permits for sorting of the analyte. Usually, aptamer binding is very specific.

By incorporating aptamers or other biomolecules to the microstructures of the SMARTS system, the system is capable of reversible, dynamic capture and release of unmodified target molecules from complex mixture. Aptamers can be conjugated on the microstructure tips, which are known to bind to a variety of target molecules including organic molecules, peptides, proteins, enzymes, viruses, and cells. Aptamers can be selected to bind to any specific molecules in each of these categories. In other embodiments, conjugate antibodies, which bind to specific corresponding proteins, can be used. Regular DNA or RNA capable of targeting complementary strands in solution (which may be attached to a larger entity) are also contemplated. Theoretically, any oligonucleotide (DNA, RNA, aptamer) or polypeptide (protein, enzyme) class can be used in the chemo-mechano-chemical ($C_1$-M-$C_2$) system, so the possibilities are quite broad. The system also can be used in the sensing and sorting of analytes in a microreactor device.

One can potentially vary a number of parameters, such as the binding energy of particles, geometry and dimension of microstructures, flow condition and the oscillation speed, to adjust/attenuate the efficiency of catch, release, and catch/release events. In one or more embodiments, at least one of the following factors can be adjusted to improve the sorting mechanism of the SMARTS system: particle-microstructure adhesion energies, the interfacial tension between the two fluid streams, microstructure stroke, the arrangement of the microstructures, geometry and dimension of microstructures, flow conditions and the oscillation speed, wetting interactions, pressure gradient, and sequential staged "catch and release".

The "catch and release" system can also be extended from biomolecules to cells; various capturing entities attached to the active tips of the microstructures can be used, whether they are aptamers, antibodies, or other biomolecules, to help select or sort cells. In one specific example, T-cell Acute Lymphocytic Leukemia cell line, CCRF-CEM, with the corresponding polyT(10)<SEQ ID:1> linked and thiol-functionalized sgc8 aptamer 5'-ATC TAA CTG CTG CGC CGC CGG GAA AAT ACT GTA CGG TTA GAT TTT TTT TTT-3'-thiol <SEQ ID:2> can be selectively bound and sorted. Thiol-modification can be utilized for surface modification of the epoxy microstructure tips as described herein. Thermal stimuli can be used to trigger configurational binding differences between the aptamer and the cell for catch and release between the top and bottom layer. The predicted Tm of the sgc8 aptamer is 33° C. which coincides well with the lower critical solution temperature, or LCST, (32° C.) of the thermoresponsive hydrogel, polyNIPAAm. The Tm of the aptamer can be confirmed by generating a melting-curve on a temperature controlled UV-Vis spectrometer. The viability of cells at temperatures close to the LCST can be determined with Live-Dead Cell Viability assays. The dynamics of the biphase microfluidic system can be adjusted for cells by utilizing minimum flow rate of the fluids to maintain laminar flow while avoiding large shear stress on the cells. Detection of cells captured in the bottom layer can be carried out by fluorescently labeling the cells and viewing them under a confocal microscope. Confirmation of the sorting capability of the microfluidic device for cells can be carried out using controls that include a system non-functionalized with aptamer and one functionalized with a mis-sense aptamer non-specific to the particular leukemia cell line.

Robotics and Integration with Other Systems

An oscillating mechanical movement originating from a non-oscillatory source, and leading to autonomous motility, has considerable potential for translation into areas such as robotics, biomedical engineering, microsystems technology and architecture, among many others. The micrometer length scale, customizability and physical simplicity of SMARTS allow it to be integrated with other microscale devices, leading to far more complex self-powered, continuous or pulsed hierarchical chemomechanical systems capable of maintaining local state conditions.

Autonomous behavior leading to the homeostatic, temperature-maintaining system can be coupled with pulsed gas-generation reactions. In particular, various simple inorganic reactions can be used, such as for example catalytic decomposition of $H_2O_2$ that generates oxygen (See FIG. 16). Such process can control pressure in the system or generate motion that triggers, in turn, propulsion of particles or generates a simple, self-regulated pneumatic system.

Self-regulated gas generation can also be achieved by an exothermic gas-generating biochemical reaction that can be triggered either by a biomolecular or synthetic catalyst, whereby feedback is integrated into the system from the heat of reaction and its dissipation with the evolution of gas, which can be used for productive work, such as propulsion, solution mixing, and autonomous movement, among other applications. Exemplary gas-generating biochemical reactions include:

(i) Hydrolysis of Urea into Carbon Dioxide and Ammonia Gas Catalyzed by Urease.

$$Urea+H_2O \rightarrow CO_2+2NH_3$$

In the presence of urea, 1 unit of the enzyme urease is able to generate 1.0 μmole of $NH_3$ per minute at pH 7.0 at 25° C. The change in enthalpy of this reaction is 61 kJ/mol. The microstructure tips can be functionalized with urease in pH 7.4 tris-HCl buffer, similar to how the tips are functionalized with the enzyme luciferase for the bioluminescent reaction described above.

(ii) Decomposition of $H_2O_2$ into Water and Oxygen Gas Catalyzed by Catalase.

One unit of catalase obtained from bovine liver is able to decompose 1.0 μmole of $H_2O_2$ per minute at pH 7.0 at 25° C. The change in enthalpy of this reaction is 100 kJ/mol. Similar to urease and luciferase, the enzyme catalase can also be deposited on the microstructure tips in pH 7.0 PBS buffer.

(iii) Fermentation of Sugar to Generate $CO_2$ Gas by Yeast.

The yeast species *Saccharomyces cerevisiae* for example can be used to ferment the sugars fructose, galactose, and maltose, each of which has an estimated enthalpy change of 134 kJ/mol, 134 kJ/mol, and 268 kJ/mol respectively. Each of these reactions produces $CO_2$ gas as a byproduct, the amount determined by the size of the sugar, where maltose would produce twice as much $CO_2$ gas as either fructose or galactose. The yeast will be allowed to adhere to the microstructure tips under starvation conditions, in the presence of collagen. Under these conditions, yeast readily adheres to underlying substrates.

(iv) Methanogenic Bacteria Generating Methane Byproducts

Figures 26A, 26B:
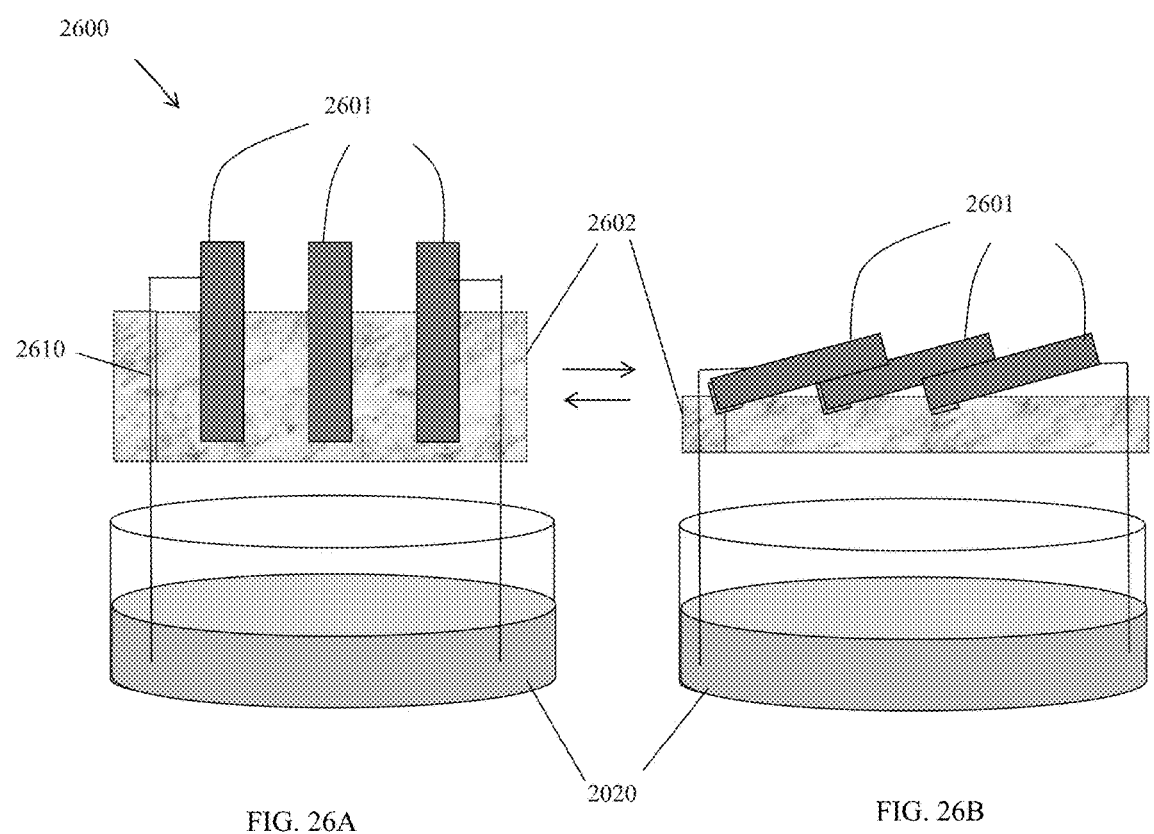
FIGS. 26A and 26B are schematic illustrations of an electrical switch that is turned on by contact of the conducting microstructures upon bending to close the electric circuit according to one or more embodiments.

In some embodiments, the microstructures may be used as a switch in circuits and other devices. For example, when the micro/nano/macro-structures embedded in gel are conducting, they can come in contact upon bending and close the electric circuit. Upon gel expansion, the circuit is disconnected, as is shown in FIG. 26. FIG. 26A shows a switch 2600 made from structures 2601 embedded in hydrogel 2602. In the inactivated state (FIG. 26A), the individual structures are not in electrical contact. Upon activation by contraction of the hydrogel (FIG. 26B), the microstructures move into bending contact with one another. An electrical contact 2610 to an external device 2620 completes the switch. In principle, the switch can be coupled with any responsive gel and utilized as an on/off switch that may or may not use an additional external electricity source (a battery) and even be coupled with another electrochemical reaction in the external loop. Oscillatory, or rather periodic, switching applies to both autonomous and externally driven SMARTS.

Figure 28:
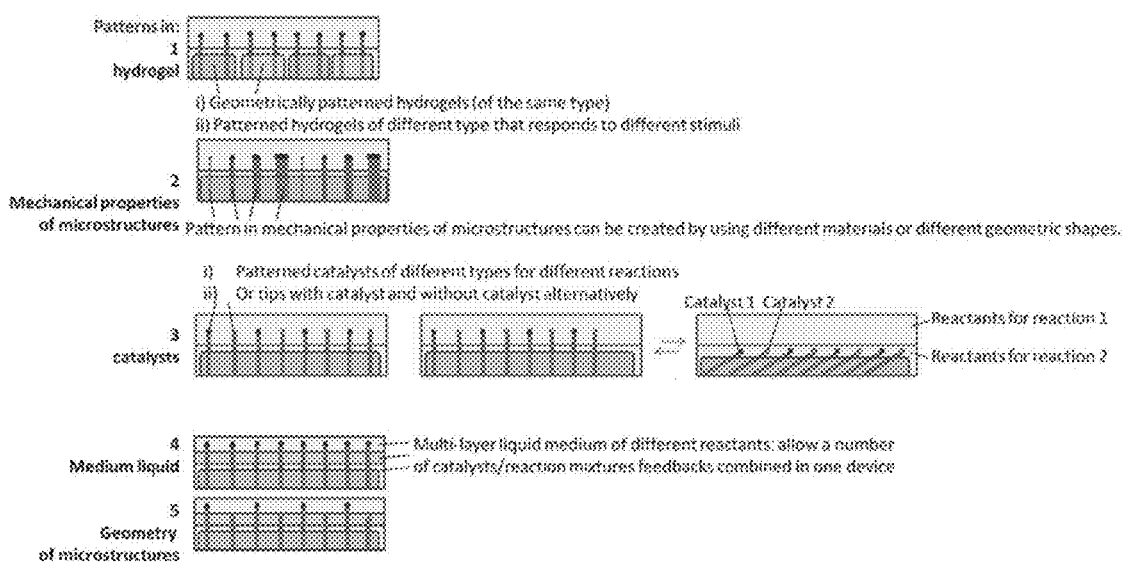
FIG. 28 is a schematic illustration showing variations in the device including variations in hydrogel patterning (1); microstructure patterning (2), including mechanical properties, shape and composition; catalyst patterning and chemistry (3); and conceptual multi-liquid-layer designs of the device (4-5).

Patterning can be used to generate controllable wave-like patterns of bending/movement of the microstructures and/or of the top layer above them that can be used for particle propulsion, for example. FIG. 28 illustrates the various types of patterning that can be implemented to create a variety of actuation patterns. In #1, different hydrogels are used to create geometrically patterned hydrogel. For example, the hydrogel can be the same, and be placed in patterns to cause microstructures to deflect in a specific location on the device. In other examples, more than one type of hydrogel can be used, each of which has a different trigger condition, Thus, the device can be designed to provide actuation of microstructures under differing conditions linked to the different actuation conditions of the different hydrogels. Patterned (hydro)gels will cause some ordered patterns of movement of microstructures.

In other embodiments, the mechanical properties of the microstructures themselves can be patterned, as shown in FIG. 28, #2. For example, the microstructures can be made of different materials having different mechanical strengths. In other examples, the microstructures can be made having different thicknesses or shapes that also provide differing mechanical properties.

The devices can also be decorated with different catalysts, as illustrated in FIG. 28, #3. The system also can be patterned to have some tips with catalysts and others without any catalyst. Devices are provided that permit different reactions to occur within different regions or at different times in the device. For example, a system is provided having two different catalysts, one that is active in the first upper phase of the device and the second that is active in the second lower phase of the device. As the hydrogel cycles between the contracted and expanded states, the microstructures move between the first and second phases, each of which initiates a different catalytic reaction.

FIG. 28, #4 illustrates another embodiment of staged catalysis. In this embodiment, several layers of liquids are employed. The liquid phases may separate due to for example differences in density or compatibility. Each liquid layer can include a set of reagents that are triggered by a different catalyst, thereby permitting a number of different reactions to take place in the device. As discussed herein, a reaction on one layer can be used to trigger a reaction in one or more of the several layers in the device. This permits a number of catalyst/reaction medium combinations and feedbacks in the same device.

Lastly, geometrically patterned microstructures of different heights and shapes can also trigger different reactions to occur in different layers, as illustrated in FIG. 28, #5. For example, one pair of catalyst/reactants creates homeostasis (as the thermal system does) by having autonomous oscillation. This can bring the second catalyst in and out of a second layer that creates bioluminecense to create intermittent light.

Separately, when the patterned deposition of different catalysts within the same system is realized, one can combine the temperature homeostatic character of the base system with a secondary (tertiary rather) reaction that will take place in the bottom (aqueous) layer when the structures carrying the second catalyst are dragged into the bottom layer (by the contraction of the gel when T>LCST) that can now contain the fuel for this tertiary reaction. This will allow mixing and matching and switching on/off a number of reactions, including biochemical ones in a static system rather than in a microfluidic channel. In one embodiment, an autonomously blinking device is provided with bioluminescence in the bottom layer being switched on and off due to (slaved to) the temperature-responsive feedbacked SMARTS. Other (tertiary) reactions with macroscopically detectable outputs (not just light) should be possible as well. All the five cases schematically presented in FIG. 28 can be mixed and matched, by which a number of catalysts/reaction mixtures feedbacks can be in principle combined in one device that may be slaved to the homeostatic one.

Figure 29:
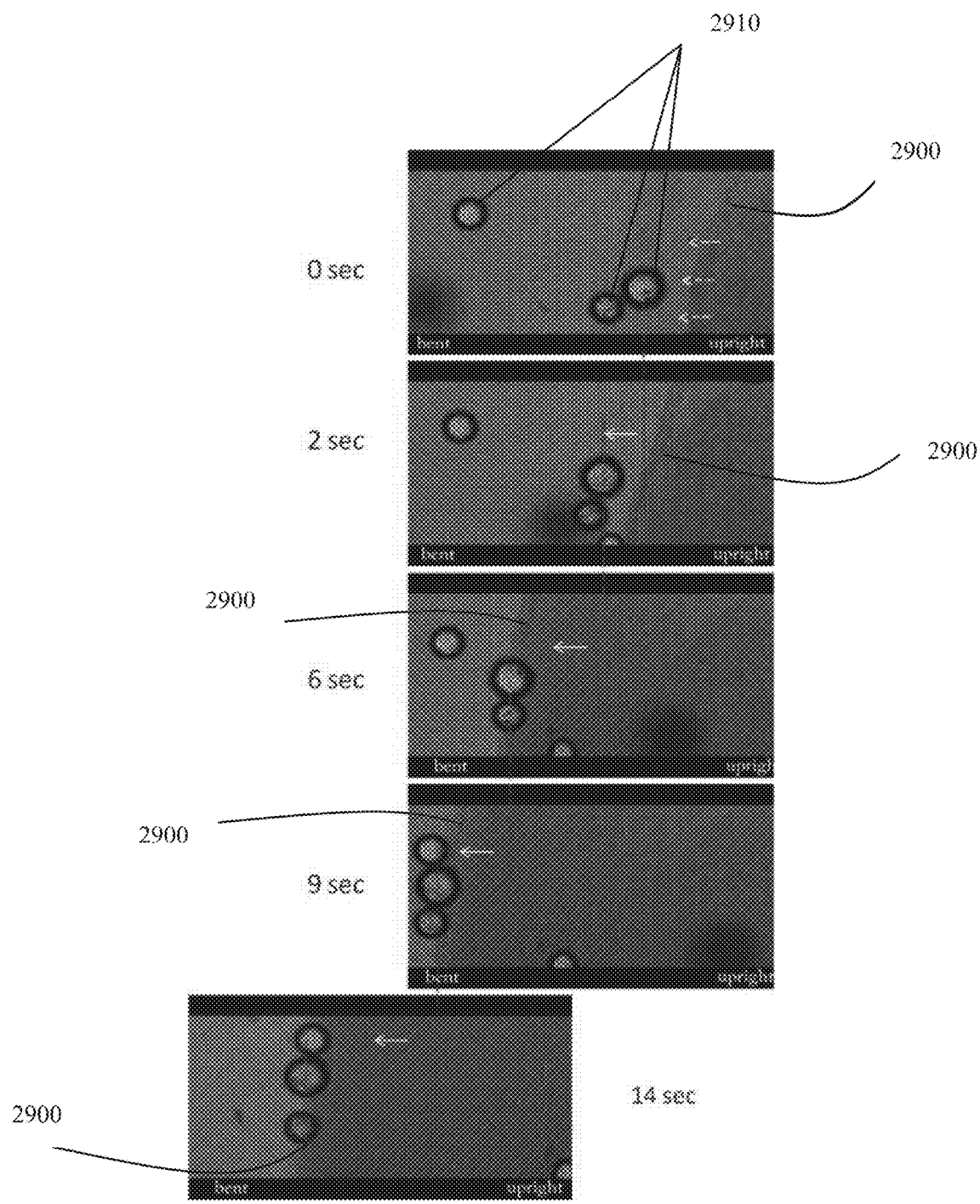
FIG. 29 is a series of photomicrographs illustrating propulsion of particles across the device surface.

In other embodiments, the actuation of the microstructures can be designed to create a force that moves objects within the device. Microparticles can be propelled by the profile/gradient of the actuating microstructures driven by the interface of patterned horizontal-bilayer liquid medium, which can be created by using electrical field within, for example. a microfluidic device, mostly by bending and in the same direction as the bending. Microparticles can be propelled by the profile/gradient of the actuating microstructures driven by the interface of patterned horizontal-bilayer liquid medium, which can be created by using electrical field. In one example, particles 2910 were placed in a system containing hydrogel-embedded microstructures, as shown in the microscope images in FIG. 29. Glass microparticles of 20-100 micrometer diameter are placed on top of the surface of microfins embedded in pH-responsive hydrogel. The sample is immersed in the liquid medium that has pH gradient. The microfins are upright at pH>pKa (transition pH for pH-responsive hydrogel, which is 4.25 for polyAAc-co-polyAAm gel in this study) and bent at pH<pKa. If the pH gradient is moving in the bath, especially when the pH in one location changes from >pKa to <pKa, then the originally upright microfins start bending, which can propel the particles on these fins to move in the direction same as the bending. The microfins form an interface moving along with the moving interface in the liquid medium with pH=pKa. Hydrogel activation was initiated in a wave starting at the right side of the image. The front is indicated by notation 2900, as it moved across the device. The pH gradient can be formed by different methods, for example, 1) by electrical field with electrolyte medium placed between two electrodes, or 2) by microfluidics with acidic and basic solutions, 3) by injecting basic solution into acidic solution, or 4) by patterned hydrogel or microstructures, to name a few. When the particles were hit by the swelling/contracting interface of hydrogel, they started to move and usually stayed with and move along the interface. A higher degree of control of the particle propulsion can be conducted by patterning hydrogel, microstructures, or liquid medium and with particles of different sizes, densities, materials, electric affinities if electrical field is employed for creating the bilayer liquid interface, as is hereinabove.

The chemo-mechano-chemical ($C_1$-M-$C_2$) system exhibits the capability of regulated energy interconversion via three key components: Input signal→Control center: Mechanical movement→Output signal, in the form of both single direction and feedback loop. Both the input and output can be diverse types of energy, leading to a large variety of the functions and applications. The potential applications of such systems are listed from the following three aspects.

1. From the Aspect of Stimuli or Input Signal:

Thermal-regulated systems: As is demonstrated with temperature-responsive hydrogel coupled with exothermic reaction, the local/system temperature is regulated around the LCST of the gel within ~3 degree precision (the amplitude of the temperature oscillations can be either increased or dampened, if so desired, by appropriate tuning of the system). It can use an endothermic reaction, when the environment temperature is higher than the LCST of gel, so that the temperature can be regulated by cooling via reaction and heating via environment.

pH-regulated systems: The local ion (proton/anion/cation) concentration in the liquid medium can be regulated by SMARTS when pH-responsive gel and acid- or base-producing reactions are employed.

Glucose/Biomolecule-regulated systems: Similarly, when glucose-responsive hydrogel is used, SMARTS can detect or even self-regulate the local glucose concentration, as an indicator, detector, or sorter.

Light-regulated systems: The hydrogel can be light-responsive at certain wavelength. Similarly, SMARTS can be regulated by light signals, and more interestingly, the microstructure can be individually, locally controlled by comparable-sized light/laser spot. It provides more flexibility and higher level of control of the (self-)regulation.

2. From the Aspect of Output Signal:

Thermal regulation: SMARTS is a great thermal-regulator. In this way, the reconfigurable adaptive device can help regulate and control the temperature on surfaces that are prone to thermal energy fluctuations or that require strict thermal consistency. These include thermostats for biological cell culture, microreactors that maintain the user-defined temperature in a narrow range, autonomously and without external energy sources. It can be incorporated into thermo-adaptive windows that respond to deviations from the desired temperature range in both directions—positive and negative. It can be used to maintain the comfortable temperature in the pieces of footwear, like insoles—reusable or even disposable.

Furthermore, as a reconfigurable thermo-responsive device, it can be coupled to other devices that utilize heat, such as a thermoelectrical cell (TEC), which harnesses heat and turns it into electrical work, serving as thermo-voltaics as the counterpart of photovoltaics in solar cells. Such a coupling can introduce greater control into and enhance the overall utility of a thermionic energy converter.

Gas generation: the controlled pulse gas generation with $O_2$ producing reaction, Pt-catalyzed $H_2O_2$ decomposition has been demonstrated. Many other gas producing reactions can be employed. The pulse gas may be useful for propulsion, repulsion, mixing, as a pneumatic device or other applications.

Pulsed light generation: SMARTS can produce light output signal in a controllable manner, for example, by i) applying fluorescence dye on microstructure tips and a quencher in the top $C_2$ layer. In this case, light is generated in the bent state of the microstructures and disappears through controlled quenching when introduced in the top reaction layer, ii) applying light producing reactions as $C_2$, such as (bio)luminescence reaction. In this case, light is generated when the structures are in their upright orientation and enter the reaction medium that switches fluorescence upon contact with the reactive tip, and light is switched off again when the microstructures bend, or iii) using semiconducting materials in the place of epoxy under excitation, photoluminescence polymers or other inorganic materials that are widely used in LEDs or photovoltaics.

Light-driven cargo control: UV light triggers cargo drop-off, for instance, for Streptavidin-Biotin, pathogen, aptamer-target molecule bindings. Two routes for cargo release, metal (e.g. silver)-dissolution assisted and photocleavable bifunctional linker (PCL)-assisted cargo drop-off, could be employed. In each route, irradiation of UV light of appropriate wavelength, e.g., 365 nm. snaps the link holding the preformed motor-cargo doublet, releasing the cargo.

Silver chloride (AgCl) particles in the presence of UV light and dilute hydrogen peroxide exhibit both single-particle and collective oscillations in their motion which arise due to an oscillatory, reversible conversion of AgCl to silver metal at the particle surface. When silver chloride is exposed to UV light in water in the absence of $H_2O_2$, it decomposes through a multistep pathway that yields the following net reaction.

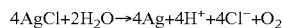

$$4AgCl + 2H_2O \rightarrow 4Ag + 4H^+ + 4Cl^- + O_2$$

In deionized water, the resulting protons and chloride ions induce motion of the AgCl particles through diffusiophoresis. A large range of light-induced reactions can be applied on SMARTS and will convert the chemical input via the mechanical movement into many other forms of output signals.

Controlled electric conduction: Based on the platform/design of SMARTS, when the top layer liquid medium is a conductive material, or it has a solid conductive confining surface on the top of device and the tips of microstructures are also modified with conductive materials, the electric conduction of the surface or the whole system can be controlled by chemically-induced mechanical actuation of the microstructures. The switchable conductivity of the thin film can be useful and, moreover, it can be employed for additional electrochemistry, such as the controlled electrochemical synthesis of conducting polymer and other wide variety of electric-induced chemical or physical processes.

Electronics: In SMARTS, when piezoelectric materials that convert mechanical energy into electric energy are used in the place of epoxy, the system will be capable of controlling the electrical signal generation, exhibiting chemo-mechano-electric interconversion process. This new, adaptive system can serve as a broad, novel platform, based on which a variety of new functions could be explored.

SMARTS is the first artificial materials system possessing homeostatic ability, as well as the first to achieve chemo-mechano-chemical feedback loops. This strategy offers profound opportunities for creating next-generation materials that enable the design of self-regulating autonomous feedback systems. A large diversity of homeostatic systems can be designed with various regulatory functions (pH, light, glucose, etc.) for advanced energy-efficient, "smart" materials and devices. The micrometer length scale and physical simplicity of SMARTS allow it to be integrated with other nano/microscale devices for incorporation into unique bottom-up hierarchical chemo-mechanical feedback systems, providing a basis for the design of far more complex self-powered, tunable, or pulsed mechanical motions and excellent maintenance of local state conditions. The controllable self-oscillatory motion, signal switching, unique energy conversion, and the capability of integration with microfluidic, sensory devices provide a transformative basis for engineering chemo-mechanical self-regulation and feedback into systems ranging from thermo-voltaics, controllable microreactors, temperature-regulators and antifouling materials.

The adaptive device can be utilized for various applications broadly as an actuator in response to many external stimuli (pH, temperature, light, humidity, magnetic or electric field, electron transfer), either individually or in combination thereof. A non-limiting list of potential applications includes:

The device responds to changes in external heat and interacts accordingly by either allowing the excess heat to dissipate, or by compensating for low external temperatures by generating heat through a catalyzed reaction (e.g. hydrosilylation). In this way, the reconfigurable adaptive device can help regulate and control the temperature on surfaces that are prone to thermal energy fluctuations or that require strict thermal consistency. A variety of other catalytic reactions can be employed. Furthermore, as a reconfigurable thermo-responsive device, it can be coupled to other devices that utilize heat, such as a TEC, which harnesses heat and turns it into electrical work, serving as thermo-voltaics as the counterpart of photovoltaics in solar cells. Such a coupling can introduce greater control into and enhance the overall utility of a TEC. Also, such device can provide colorimetric information of different reactions, acting as a sensor for the presence of a variety of chemicals in the atmosphere or in solution, simply by depositing the corresponding catalysts or reagents on the tips of the microstructures. Furthermore, the use of catalysts in the device allows one to use them in a fine control over highly exothermic reactions in a microreactor setting.

The device can be used for sorting purposes, or as a bio-sensor, by conjugating certain aptamers to the microstructures. By modifying the aptamer of interest, one can turn the oligonucleotide into a pH-sensitive or temperature-sensitive strand that is able to bind/release a target molecule according to the local pH or temperature. The biphasic design can be used to sort molecules from the upper stream where the aptamer would bind strongly with a specific molecule, protein, or even cell of interest and subsequently release the target molecule into the bottom stream where the local pH or temperature would loosen the hold the aptamer has on the target molecule. By integrating the many merits of the stability, and specificity of aptamers for a diverse array of target molecules, such an application can readily find use as a biosensor, a simple diagnostic tool of diseased indicators in solution (misfolded proteins, EGFR on cancerous cells), or even as a tool to quantitatively determine the extent of chirality achieved in the synthesis of a complex molecule.

3. From the Aspect of Function:

Microfluidic devices: SMARTS can be integrated into microfluidic devices, which are powerful and flexible tools for a wide range of applications, from lab on chips to medical devices. A variety of other applications in microfluidics are envisaged, such as e.g., micropumps, valves and switches. In other applications, the devices can be incorporated into structural materials that maintain temperatures such as windows, walls, and roofs.

Bio(medical) related or Diagnostics: The molecular-level chemical signals can be amplified by using micron-scale mechanical movement and/or by other type of outputs that are converted from the chemistry with this platform of chemo-mechano-chemical (or photon, thermal) transduction, involving light, heat, proton, etc.

Colorimetrics: the device can provide colorimetric information of different reactions, acting as a sensor for the presence of a variety of chemicals in the atmosphere or in solution, simply by depositing the corresponding catalysts or reagents on the tips of the microstructures. Furthermore, the use of catalysts allows fine control over highly exothermic reactions in a microreactor setting.

Switchable Surface: "Stimuli-responsive" or "smart" materials are defined as synthetic materials that experience dramatic changes in physical and/or chemical properties when subjected to small environmental influences. These switchable surfaces have biomedical applications and can be created through the use of a single layer of molecules that spontaneously form on a surface. Surface switching typically occurs in response to environmental changes or chemical reactions which limits use. It has potential applications in biomedical diagnostics, cell adhesion/motility studies, tissue engineering, and drug delivery.

Nano/micro Cargo transport: Photochemical stimuli for the drop-off of cargo from load-bearing catalytic Pt—Au nanomotors powered by hydrogen peroxide ($H_2O_2$) fuel solutions developed by Sen. (Drop-Off of Colloidal Cargo Transported by Catalytic Pt—Au Nanomotors via Photochemical Stimuli, Small 2010, 6, 1479-1482). Applications for motors that can transport and drop-off materials in the mesoscale size regime include bottom-up assembly of structures, pattern formation, drug delivery at specific locations, and so on.

Thermovoltaics: As a reconfigurable thermo-responsive device, it can be coupled to other devices that utilize heat, such as a TEC, which harnesses heat and turns it into electrical work, serving as thermo-voltaics as the counterpart of photovoltaics in solar cells. Such a coupling can introduce greater control into and enhance the overall utility of a thermionic energy converter, or TEC.

The device can be used as a thermostated (heated) surface for biological studies (cells) and related processes that can be performed on a small scale outside incubator. It can be incorporated into thermo-adaptive windows that respond to deviations from the desired temperature range in both directions—positive and negative. It can be used to maintain the comfortable temperature in the pieces of footwear, like insoles—reusable or even disposable.

These and other aspects and embodiments of the disclosure are illustrated and described below.

Sample Preparation:

Silicon masters of the microfin and micropost arrays were fabricated using the Bosch process that is very well familiar to those skilled in the art. The microfins were staggered array of 2 µm wide, 10 µm long and 18 µm tall plates with 5 µm spaces. The microposts are square array of 10 µm diameter and 100 µm tall posts. Silicon masters were then fluorosilanized with (tridecafluoro-1,1,2,2-tetrahydrooctyl)trichloro silane in a desiccator under vacuum at room temperature for at least 24 hours to facilitate demolding of the PDMS from silicon masters.

PDMS prepolymer in a 10:1 (wt./wt.) ratio of base resin:hardener was mixed for 3 minutes and degassed under vacuum at room temperature. To create negative replicas of the silicon structures, the PDMS prepolymer mixture was poured over the fluorosilanized silicon master in a petri dish, put under vacuum again to remove residual bubbles, and then cured for 2 hours at 70° C. After cooling, the silicon masters were demolded by peeling off the PDMS molds. To make a polymer replica, a few drops of a 9:1 (wt./wt.) prepolymer mixture (UVO-114:GMA) were placed on the PDMS mold and a glass slide was put over the prepolymer to serve as a flat backing to yield an area of polymer with a coverage of about 4 cm2. The prepolymer mixture was cured under a UV lamp (100 W, Blak-Ray with a 365 nm bandpass filter, ~10 mW/cm$^2$ at 365 nm) for about 20 minutes. The glass slide was then slowly demolded from the PDMS mold to yield an array of polymer structures that were an exact replica of the original silicon master. A 100% UVO-114 prepolymer was used to make the confining surfaces using the same replication procedure. To form hydrogel films on microfin structures by shadow curing of a UV-initiated hydrogel precursor solution, a drop of hydrogel precursor solution (4 µL or 20 µL) was placed on the freshly-prepared microfin surface of 0.5×8 mm area in the case of pH-responsive gel or 8×8 mm in the case of temperature-responsive gel, a cover slip was laid over the droplet to cover the solution, and the sample was cured under a broadband UV illumination (~10 mW/cm$^2$) for 5 minutes.

Functionalization of the microstructures' tips with fluorescence dye fluorescein, enzyme luceferase, and $H_2PtCl_6$ catalyst was accomplished using stamping method. See, FIGS. 6 and 7. Hydrogel-embedded microstructure was treated by $O_2$ plasma for 30 seconds to form reactive epoxide and hydroxyl groups on the epoxy tips. A flat PDMS stamp inked with catalyst solution was brought into contact with the top surface of microstructure gently. The solutions used for stamping were as follows:

a) for the fluorescence quenching, 100 mg/L fluorescein in 1:1 v/v water:ethanol;

b) for the bioluminescence reaction, 1 µmol/L lyophilized luciferase in 0.5 mol/L HEPES buffer of pH 7.5 at −4° C.;

c) for the hydrosilylation reaction, 1 mg/mL $H_2PtCl_6$ in DI water; and d) for "click" reaction, 50 mg/mL $Cu(PPh_3)_2NO_3$ in chloroform.

The stamp was left on microstructure surface overnight to let the water or solvent completely evaporate, leaving the catalyst or dye attached to the epoxy surface through covalent bond and/or non-specific absorption. The unbounded catalyst was washed from the sample surface by thorough rinsing with water or buffer. The tip fictionalization is demonstrated by immobilizing fluorescent dye on the top surface of the microposts. The selective modification of the microstructures, visualized by fluorescence microscopy, enables the precise control of the occurrence and ceasing/termination of the reaction on the top layer of the SMART system.

The precursor solution pH-responsive hydrogel is 20% AAm, 20% AAc, 2% crosslinker bis-AAm and 1% UV-initiator Irgacure® 2959 by weight in deionized water. 10% w/v dodecyl acrylate was added in the pH-responsive hydrogel precursor solution with water replaced by dimethylformamide (DMF, Aldrich Sigma), in order to increase the transition pH of the hydrogel from 4.25 to 7.0 for the purpose of conducting luciferase enzymatic reaction at pH range of 6-9.3 All samples were soaked in deionized water for 30 minutes after hydrogel curing to swell the hydrogel before the removal of the confining surface.

The precursor solution temperature-responsive hydrogel is 40% NIPAAm with 2% crosslinker bis-AAm and 0.5% UV-initiator Darocur® 1173 in DMSO. Temperature-responsive hydrogels after photocuring were soaked in DIW for overnight to replace DMSO with DIW for maximum swelling ratio by temperature change.

Optical imaging and video recording were done on an Olympus IX71 inverted microscope using StreamPix v.3 software and QImaging EXi Blue and Evolution VF cameras. Samples were sputter coated with Pt/Pd for imaging with a JEOL JSM 639OLV scanning electron microscope. Time resolved temperature of SMARTS with exothermic reactions was tracked by precision fine wire thermocouples (Omega) connected to a temperature controller and a computer. The LCSTs of the temperature-responsive hydrogels, pNIPAAm and 5% BMA-pNIPAAm, were measured by Differential scanning calorimeter (TA Instruments, Q2000).

Example 1

A Self-Modulated Adaptively Reconfigurable Tunable Surface (SMARTS)

A Metal Complex-Catalyzed Organic Reaction demonstrates the device ability to generate a self-regulating thermal energy cycle. For hydrosilylation reaction on SMARTS, two types of temperature-responsive hydrogel were used: pNIPAAm and pNIPAAm with 5 mol % butylmethacrylate (BMA). The LCST of the gel without and with 5% BMA are 32 and 29° C., respectively, measured by DSC and weighing the gel that soaked in water at different temperature. The hydrosilylation reagent solution was 1-hexene: triethylsilane at 1:1 (by mol, both in liquid form). The microstructure tips were functionalized by contact printing the HAIRS with a flat PDMS stamp inked with 1 mg/mL $H_2PtCl_6$ aq. solution. For the SMARTS with static liquid medium, 8×8 mm square reservoir was made by polyacrylic spacer and encapsulated by placing a cover slip on the top. The hydrogel-embedded microfins in the reservoir were immersed in 1.85 μL reagent solution (~30 μm thick liquid) in the top phase and 1 μL DI water in the bottom phase. The biphasic liquid interface in a reservoir was tuned such that the interface occurred at such a height that the tips of the nano/microstructures were exposed to the top fluid layer when upright and, in contrast, exposed only to the bottom fluid layer when bent.

Figure 8:
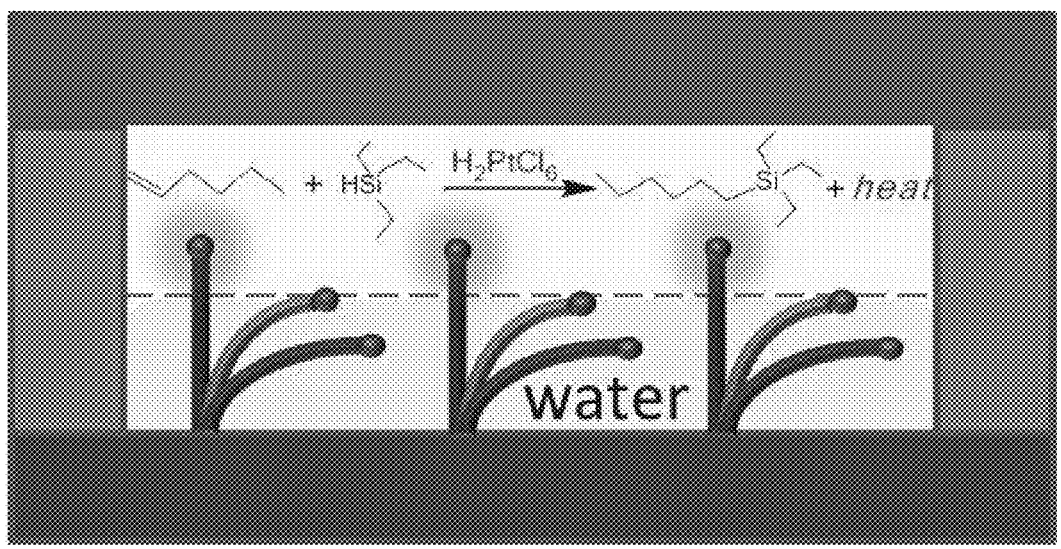
FIG. 8 shows the configuration and schematic of a thermo-responsive device according to one or more embodiments as applied to the hydrosilylation reaction between 1-hexene and triethylsilane catalyzed by hexachloroplatinic acid immobilized on the tips of the microstructures that are brought in contact with the reagent layer upon expansion of the gel, which supports the microstructures.
Figure 9:
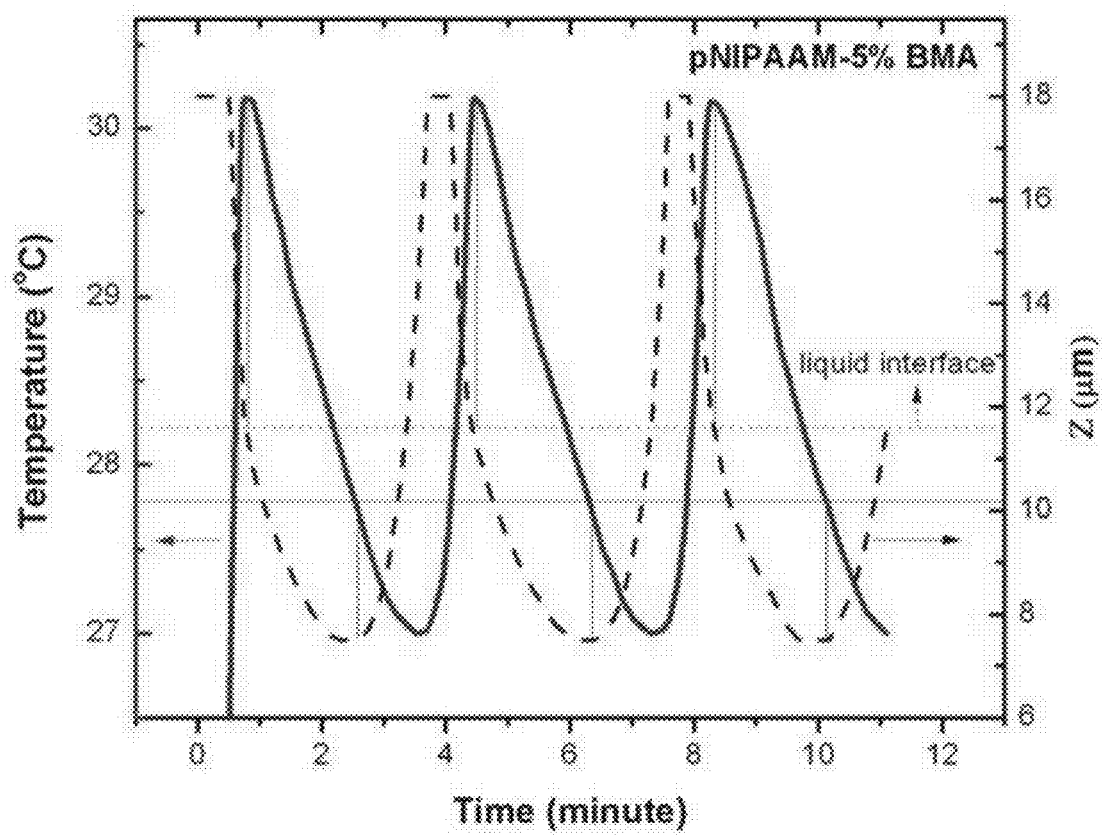
FIG. 9 is a time-resolved graph of the temperature and vertical coordinate (Z) of the tips of microfins embedded in a hydrogel of poly(N-isopropylacrylamide) (polyNIPAAM) with 5% butylmethacrylate (BMA).
Figure 10:
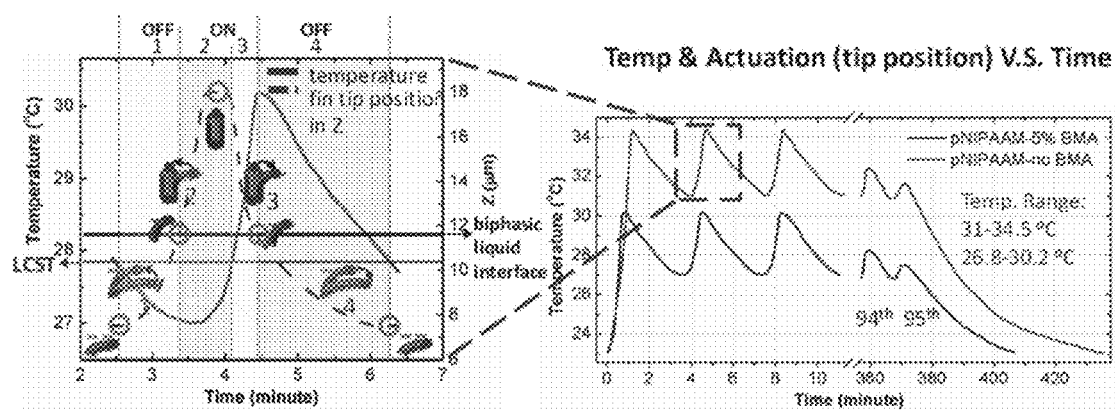
FIG. 10 shows the temperature tracking over time of a chemo-mechano-chemical ($C_1$-M-$C_2$) system using hydrogels of different components, i.e. pure poly(N-isopropylacrylamide) (polyNIPAAM) and poly(N-isopropylacrylamide) (polyNIPAAM) with 5% butylmethacrylate (BMA) that allow to stabilize temperature in different ranges.

FIG. 8 shows the configuration and schematic of a thermoresponsive device that employs an exothermic hydrosilylation reaction between 1-hexene and triethylsilane catalyzed by hexachloroplatinic acid immobilized on the tips of the microstructures. As the tips of the microstructures were exposed to the top layer containing the reagents when T<LCST, the exothermic reaction proceeded with the generation of heat. This heat caused the temperature-sensitive hydrogel to contract when T>LCST, bending the microstructures away from the reaction in the top layer and into the aqueous bottom layer. This prevented further heat generation from the chemical reaction, cooling the device down. The subsequent heat loss (either spontaneous or induced) led to a drop in temperature that caused the hydrogel to swell, again bringing the microstructure tips in contact with the top layer and generating heat. The SMARTS is a self-powered oscillation system using chemical reagents as 'fuel'. The heat generating and temperature regulating function maintain the system temperature in certain range around the transition temperature of the hydrogel used. This thermal energy cycle can easily repeat over several hours in a static reservoir, while it is able to work incessantly within the reagents if they are regularly replenished. FIG. 9 shows the specific time scale of these energy cycles, displaying the position of the tips of the microstructures as a function of time (dashed line) alongside the change in temperature of the device as a function of time (solid line). From this graph, the frequency of the energy cycles (in this case ~3.8 minutes per cycle on average) can be determined from the periodic function of temperature. Further, it can be seen that there is a ~¼-wavelength (cycle period) offset between the position of the tips in the top layer as shown by the maximum of the dashed position curve and the heat generated from the reaction as depicted by the maximum of the solid temperature curve. This shows the transition of the tip position takes place immediately at the time when the temperature goes across the transition temperature of the hydrogel and similarly, the temperature immediately stops increasing or dropping when the tip goes across the reagent/water interface. This indicates fast responsiveness of the SMARTS, which render it excellent capability of precise control of the temperature. The temperature at which the position of the tips changes direction (increasing from the minimum) is indicative of the transition temperature (as depicted by the horizontal line in the graph at around 27.7° C., in this particular case), above which the hydrogel contracts and below which it swells. Since contraction of the hydrogel takes longer than swelling, the temperature at which the tip position starts to decrease is greater than the transition temperature determined by the temperature at which the tip position starts to increase. This is characteristic of the temperature responsive hydrogel and visible in the graph. Additionally, the liquid interface of the reservoir can be estimated by the position at which the temperature starts to decline, which is when the reaction is prevented from occurring by the movement of the tips into the bottom layer. From the graph in FIG. 9, it can be seen that this interface occurs in this particular case at around 11.6 μm with the maximum height of the tips positioned at around 18 μm. While FIG. 9 shows the energy cycles in detail, FIG. 10 shows the overall lifetime of the energy cycles in a static reservoir configuration. Although the lifetime of this particular static system is about 6 hours, the lifetime of a dynamic flow system can be significantly extended, for example, by replenishing the reagent solutions and water. In order to extend the lifetime of SMARTS by replenishing the reagent solution and water, the fluids were injected at 4:1 v/v ratio through inlets into the reservoir at the sixth hour and twelfth hour with an outlet leading the old excessive liquid out of the reservoir. For comparison with the neat 1-hexene:triethylsilane reaction, 80% (vol./vol.) 1:1 (by mol) 1-hexene:triethylsilane in toluene solution and 1:1 (by mol) 1-hexene:diphenylsilane solution were also used as the top phase in identical conditions.

FIG. 10 also shows the different temperature ranges of BMA-modified temperature-responsive hydrogel as compared to an unmodified form of the hydrogel. By including 5% BMA in the hydrogel formulation, the transition temperature of the device is decreased as well as the range of temperatures over which the device is useful. This way, the transition temperature of the temperature-responsive hydrogel can be easily tuned between 20-90° C. See, e.g., J. F. Lutz and A. Hoth, Macromolecules, 2006, 39, 893-896, which is incorporated herein by reference. Different or even wider transition temperature range of hydrogel may be achieved by other methods adjusting composition or swelling ratio and using other type of temperature-responsive hydrogel, such as, e.g. poly ((ethylene glycol) methyl ether methacrylate). In short, the features and functions of SMARTS, such as operation temperature range, oscillation frequency and lifetime, can be tuned by using different types of 'fuel' (exothermic reactants) and hydrogels of different responsive temperature and swelling ratio.

The oscillation period gradually increases as the reaction progresses. While the average period was 4.20 min/cycle as shown in FIG. 9, it increased from the initial value of 3.58 to ~4.50 min/cycle as reactants depleted. To further study this phenomenon, the 1-hexene:triethylsilane mixture was diluted to 80% (vol./vol.) in toluene. This led to a lower heating rate, and the temperature reaches its maximum value of 33.5° C. after 2.4 min (about 2.7 times longer than with the neat reagents). The lower heating rate results in a slightly longer initial oscillation period (3.85 min/cycle, vs. 3.58 min/cycle with neat reaction) and smaller amplitudes in both temperature (2.3° C., 31.3-33.5° C.) and actuation (~3 μm, tip position Z=~11-14 μm).

Figure 21A:
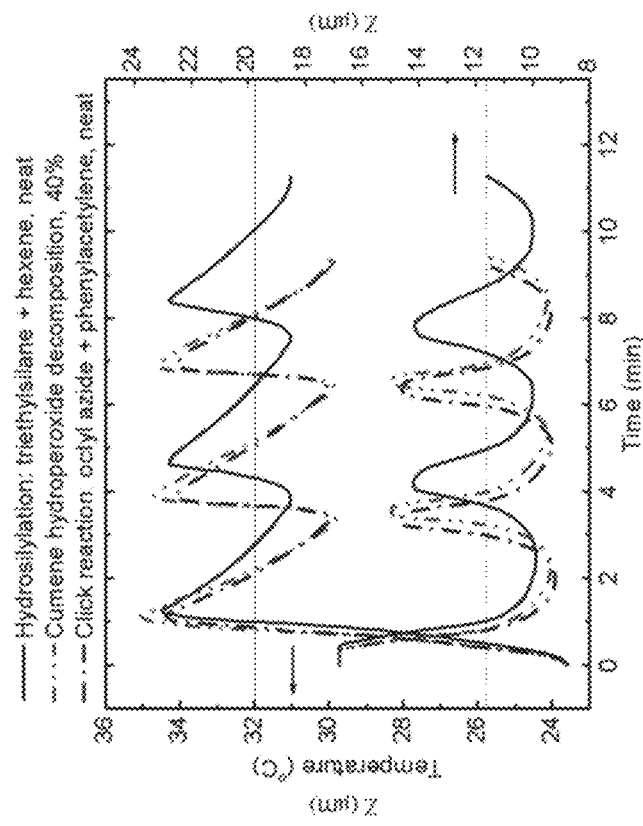
FIG. 21 shows the tuning of self-oscillation behavior of C→M homeostatic SMARTS having different heating rates resulting from different types of exothermic catalytic reactions driven by a thermo-responsive gel, in which (a) shows varying the reactant concentration and reactivity of the silane in the hydrosilylation reaction, (b) shows utilizing different classes of exothermic catalytic reactions.

When a more reactive silane, namely diphenylsilane, is used in the place of triethylsilane, the reaction is more vigorous: in comparison to the reactions that use neat or 80% triethylsilane, the relatively higher heating rate results in shorter initial oscillation period (3.20 min/cycle) and larger amplitudes in both temperature (5.0° C., 30.2-35.2° C.) and actuation (~7 μm, tip position Z=~9-16 μm). FIG. 21A includes graphs showing the time-resolved temperature and vertical projection (Z) of the tips of microfins embedded in a hydrogel of pNIPAAm, using 80% 1-hexene:triethylsilane in toluene and neat 1-hexene:diphenylsilane compared to neat 1-hexene:triethylsilane.

Example 2

Dynamic Color Switching in a Biochemical Reaction

Colorimetric/luminescent information is gathered from different chemical reactions by the implementation of the actuating device. A bioluminescent enzymatic reaction was used in which the enzyme luciferase was deposited on the tips of the microstructures. This composite structure was generated within a microfluidic channel to accommodate an aqueous bilayer, as described in FIG. 4. Laminar flow of two aqueous solutions at the top and bottom of the microfins is generated using a multilayer construction with two vertically separated inlets. By functionalizing the tips of the microstructures with the enzyme luciferase (LUC) and providing luciferin, ATP, and magnesium salt in the top fluid layer, intermittent light emission from the periodic bioluminescent reaction is created regulated by the pH-driven swelling and contraction of the hydrogel "muscle", causing the fins to move in and out of the reagent layer.

To generate the microstructures, silicon masters with an array of microfins (each fin being 2 μm wide, 10 μm long and 18 μm tall), arranged in a staggered formation were replicated in epoxy (9:1 (w/w) UVO-114 (Epoxy technology): glycidyl methacrylate). To embed microfin structures into a hydrogel film, a drop of hydrogel precursor solution was placed on the freshly-prepared microfin surface and was cured under broadband UV illumination. Because of the instability of the enzyme LUC outside of the pH range of 6.0-9.0, the volume phase transition pH of the hydrogel poly(acrylamide-co-acrylic acid) is tuned from pH 4.3 to pH 7 by introducing 10% (w/v) dodecyl acrylate co-monomer to the precursor pH-responsive hydrogel solution.

For the cyclic enzymatic reaction, fin tips were functionalized with LUC. Microfins were first treated with oxygen plasma for 30 s and then the tips were functionalized by stamping the fins with a PDMS block coated with 1 μM LUC in 0.5 M HEPES (4-(2-hydroxyethyl)-1-piperazineethanesulfonic acid) buffer at pH 7.5 overnight, leaving LUC attached to the epoxy surface through covalent bonding and/or non-specific adsorption. The unbound LUC was washed from the sample surface by rinsing with buffer. The localization of LUC to the fin tips allowed for movement of the catalyst between the two aqueous layers using the SMARTS system as the fins moved from the upright to the bent position. LUC catalyzes the oxidation of luciferin to generate light via the following reaction:

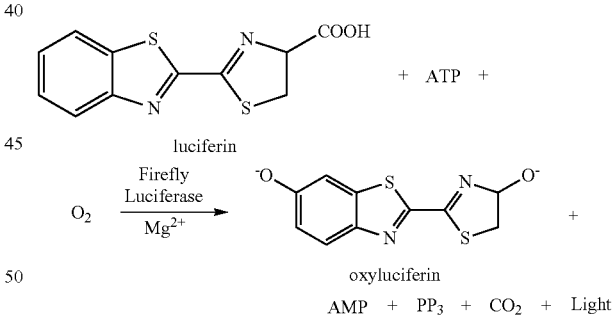

For bioluminescent enzymatic reaction on SMARTS, pH-responsive gel was used. A 1 μmol/L firefly luciferase solution was prepared by dissolving the lyophilized luciferase powder in 0.5 mol/L HEPES buffer, pH 7.5, and stored at −20° C. The reagent solution is in 0.01 mmol/L D-Luciferin sodium salt with 2 mmol/L $MgCl_2$ and 0.3 mmol/L ATP magnesium salt in 50 mmol/L HEPES pH 7.5 buffer. Lower phase is alternative flow of pH 6 sodium citrate buffer solution and pH 9. sodium tetraborate buffer solution. The reactants required for the bioluminescent reaction, including ATP, luciferin, and $Mg^{2+}$, were deposited in the top layer, leading to the emission of light when the microstructures were upright. An aqueous solution of 0.01 mM D-luciferin sodium salt with 2 mM $MgCl_2$ and 0.3 mM ATP magnesium salt in 50 mM HEPES pH 7.5 buffer was thus used in the top fluid layer as the reaction medium. The reagent solution was oxygenated and the $O_2$-permeable PDMS channel allowed further diffusion of $O_2$ for the oxidation reaction. FIG. 11 provides a schematic illustration of the reaction, and shows that the system is dark when the microstructures are not in contact with the reactants, but are self-illuminating when the tips are in contact with the upper layer. FIG. 12 is a photomicrograph of the microstructure surface in the ON and OFF states. As can be seen in FIG. 12, this reaction is not due to exogenous light and so is quite visible under extremely dark conditions. Due to the stability of the enzyme luciferase within the pH range of 6.0-9.0, the transition pH of the pH-sensitive hydrogel was tuned accordingly to occur at around pH 7.0. Above this pH, the hydrogel swells, and below this pH, the hydrogel contracts.

To create a vertically-separated aqueous bilayer, a microfluidic channel with two inlets of different depths was fabricated on top of the hydrogel-embedded microfins to form a vertical bilayer, as shown in FIG. 4. Reagent solution and water were flowed into the two inlets through the tubing at flow rates of 20 and 10 µL/min, respectively which created a laminar flow interface that intersected the heights of the hydrogel-embedded microstructures. The position of the bilayer liquid interface was determined by using confocal microscopy and was optimized to match the height of the microfins by adjusting the flow rates of the two liquids and channel height. The substrate solution was flowed in as the top fluid layer, and the bottom fluid layer was an alternating flow of pH 6.0 sodium citrate and pH 9. sodium tetraborate buffer solution, which drives the microfin actuation.

Microscopic fluorescent imaging and video recording were done using a confocal microscope equipped with an avalanche photodiode detector (APD) for quantification of the light emission. The intensity of the reaction-generated luminescence was measured from the image slides of each focal plane recorded with the APD. FIG. 13 shows the periodic change in the emitted light intensity during the actuation of the microfins; light intensity increases sharply as the tips stand upright with the flow of a pH 9 buffer in the bottom layer, and the intensity quickly decreases as the tips bend down with the flow of pH 6 buffer in the bottom layer. The rapid responsiveness and precise synchronization of the light emission and the microfin movement in and out of the reagent layer during multiple cycles are well evidenced by the time-resolved bioluminescence intensity in FIG. 13. A series of control reactions were conducted at pH 6, pH 7.5 and pH 9 in a static system. All control samples emitted light without appreciable changes in intensity, indicating that luminescence is not lost due to pH changes within the operating pH range. This confirmed that the disappearance of luminescence at pH 6 resulted from the cessation of the reaction due to the tips bending away from top reagent layer, rather than from the quenching of luminescence or dysfunction of the enzyme. The proper function of the enzyme is further supported by the sustained luminescence through 30-40 actuation cycles.

Figure 20A:
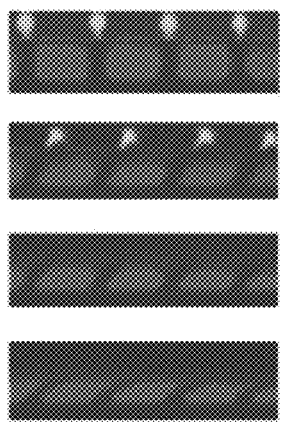
FIG. 20 shows luminescence generation observed under exogenous light and the study of dynamic configuration of microfins during actuation in laminar flow; in which (a) shows XZ sections of the fin bending dynamics at various stages of actuation and (b) shows bioluminescence intensity as a function of the vertical (Z) and horizontal (X) projection of the tips under the same condition as in a. Error bar represents standard deviation, n=4.
Figure 20B:
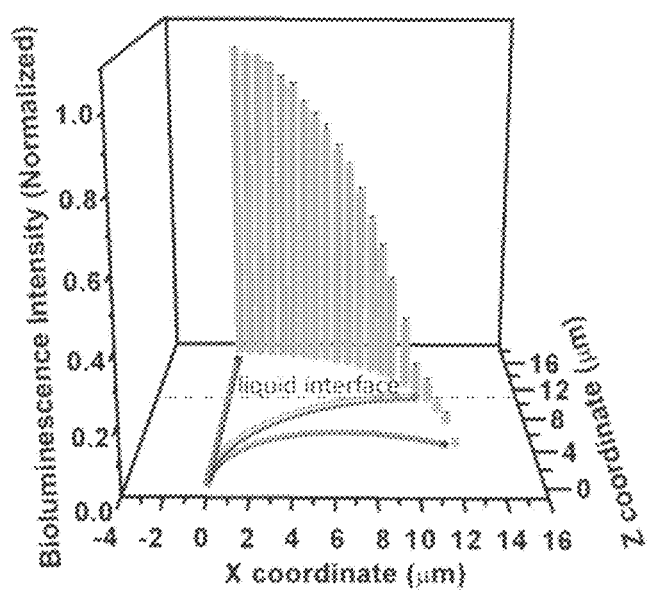

To study the modulation process of the biochemical processes via the mechanical motion, side-view configuration images of SMARTS were generated using confocal XZT scanning and fluorescent, rhodamine-conjugated hydrogels as shown in FIG. 20A. The cross-section images clearly reveal the fin tips in X- and Z-coordinates during all stages of actuation and allowed correlation the intensity of emitted light at those points of actuation as shown in FIG. 20B. This example importantly shows the robustness of the device, proving it is amenable to biological constraints and sensitive enough to show the weak bioluminescence triggered by the movement of the microstructures into the top layer.

Example 3

Quenching of Fluorophores

Figure 14A:
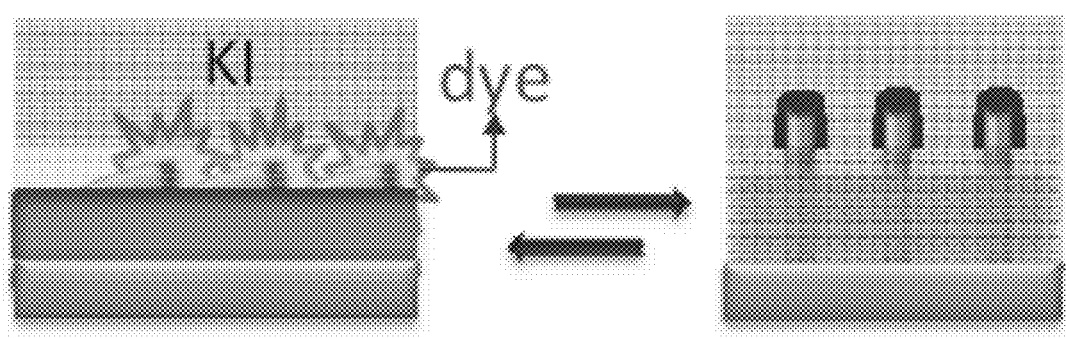
FIG. 14A is a schematic illustration of a chemo-mechano-chemical ($C_1$-M-$C_2$) system according to one or more embodiments used to cyclically quench the fluorescence of fluorescein.
Figure 14B:
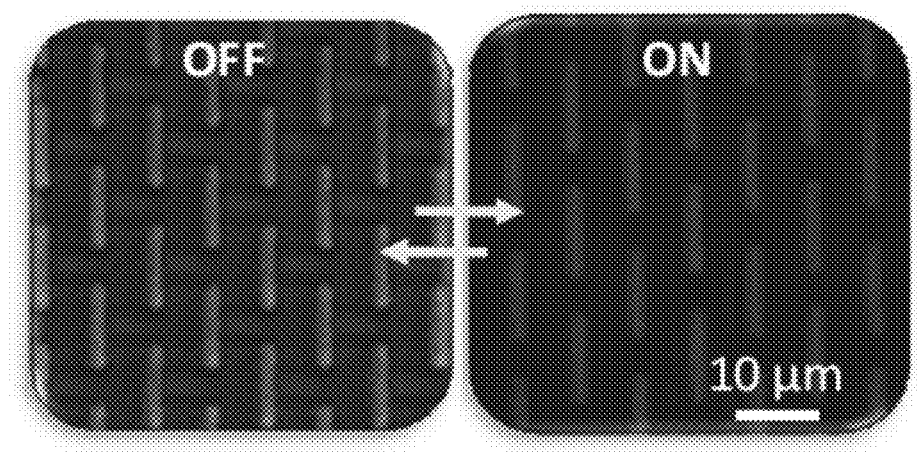
FIG. 14B is a photomicrograph illustrating experimental quenching of the fluorescence of fluorescein-treated microstructure tips when exposed to the appropriate reactants (potassium iodide—KI).
Figure 15:
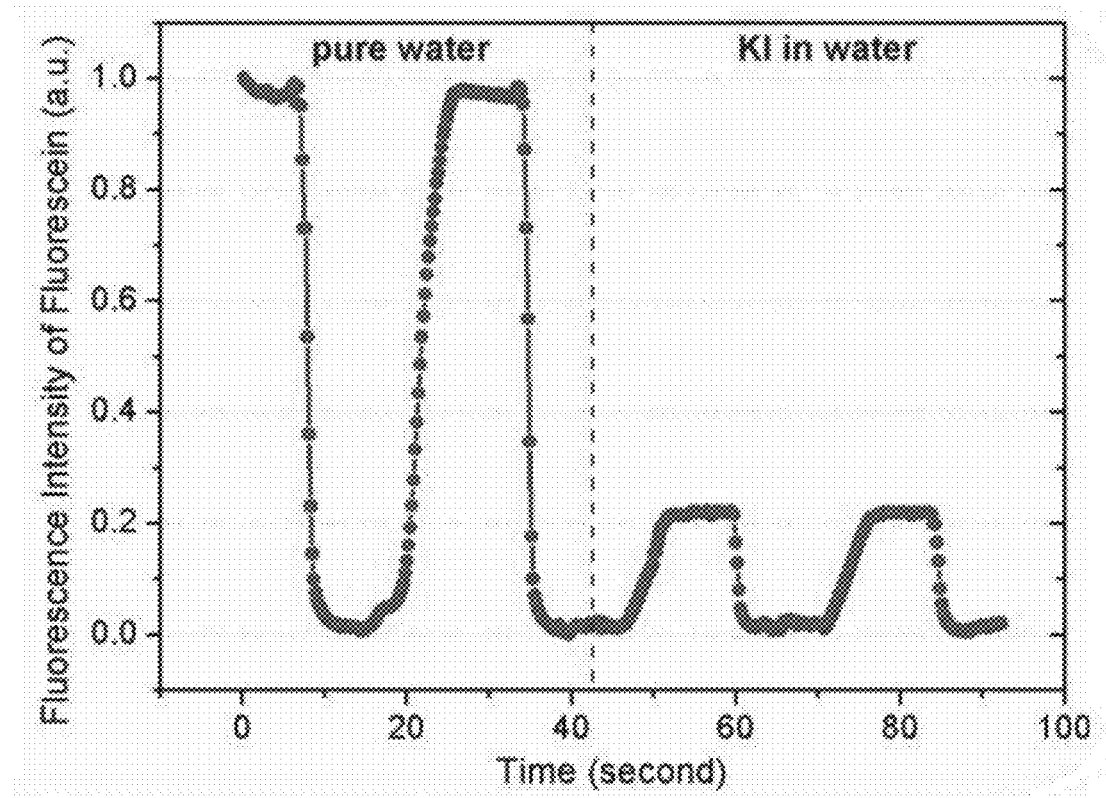
FIG. 15 is the time-resolved fluorescence intensity at the Z level of the maximum height of microfins when pure DI water is used as a control and subsequently KI in water is used to quench the fluorescence flowing through the microfluidic channel.

The quenching of fluorophores that are immobilized on the tips of the microstructures can also be visualized as they switch between the bottom aqueous layer and the top layer containing potassium iodide in deioinized water, as shown in the schematic illustration in FIG. 14A. Microscopic fluorescent imaging and video recording were done on a confocal microscope (Leica DMI3000 SP5 TCS) using a 40× oil immersion objective and Avalanche photodiode (APD, its signal is proportional to the real light intensity). FIG. 14B shows that the system fluoresces when the microstructures are bent and not in contact with the reactants (OFF state)— the tips of the titled blades show bright green fluorescence, and the fluorescence is quenched when the tips are in contact with the upper layer (ON state)—no green fluorescence is observed. For fluorescence quenching on SMARTS: The reagent solution in upper phase is 0.6 mol/L KI aq. solution. Lower phase is HCl aq. solution of pH 3 or NaOH aq. solution of pH 6, alternatively flowing in microfluidic channel, in order to drive the periodic actuation of hydrogel-embedded microstructures. Potassium iodide, a known quencher of fluorophores, and fluorescein were used in this example. As such, when the tips of the microstructures, on which fluorescein is immobilized, were exposed to the top layer, fluorescent intensity was quenched in the presence of potassium iodide in the top layer. However, if the top layer consisted of only pure water without potassium iodide, the tips of the microstructures exhibited regular fluorescence intensity characteristic of the fluorophore fluorescein. Actuation of the microstructures into the top and bottom layer was controlled by alternatively flowing aqueous acid or base in the bottom layer, inducing the swelling and contraction of the pH-responsive hydrogel that surrounds the microstructures so that this is not a self-regulating system. Also evident in FIG. 15 is the significant quenching (by 80%) of fluorescein in the presence of potassium iodide in the top flow as opposed to undisturbed fluorescence in pure water. This example utilizes fluorophores as sensors in the actuating device showing the level of control easily achievable in the biphasic reconfigurable system.

Example 4

Pulsed Gas Generation in a Catalytic Inorganic Reaction

Figure 16A:
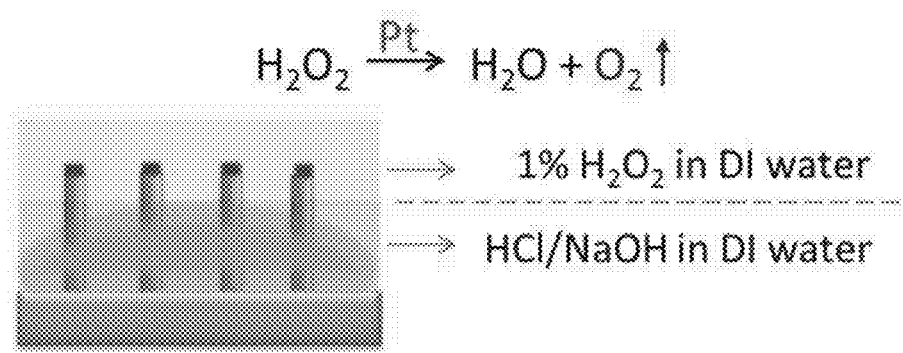
FIG. 16A is a schematic illustration of a chemo-mechano-chemical ($C_1$-M-$C_2$) system according to one or more embodiments used in an exemplary inorganic reaction to catalyze the decomposition of hydrogen peroxide when exposed to Pt catalyst.

In this example, gas bubbles were generated as an indication that a chemical reaction occurred only as the tips of the microstructures were exposed to the top layer in the biphasic system. The reaction used was the platinum-catalyzed decomposition of hydrogen peroxide into water and gaseous oxygen. For Pt catalyzed hydrogen peroxide decomposition on SMARTS: The reagent solution is 0.5-1% $H_2O_2$ aq. solution. Lower phase is the same as for fluorescence quenching in Example 3. FIG. 16A provides a schematic illustration of the reaction, and shows that the system produces oxygen gas when the Pt coated tips are exposed to $H_2O_2$. Metallic Pt deposition on fin tips for $H_2O_2$ decomposition was accomplished by depositing 100 nm thick Au as a sacrificial layer and subsequently a 100 nm thick Pt layer on PDMS mold containing negative microfin array by thermal evaporator, after which the top layer of metal was removed by scotch tape repetitively in order to retain the metals only on the fin tips. The epoxy replica with Au/Pt on top surface of tips was molded from the PDMS mold, and the Au layer was removed by etching with HF, leaving only Pt on the epoxy fin tips.

Figure 16B:
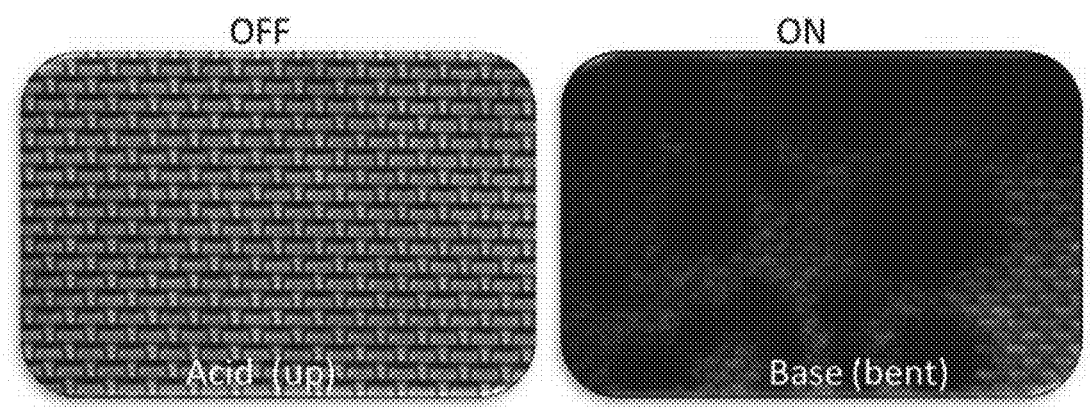
FIG. 16B is a photomicrograph illustrating the experimental system where gas bubbles were generated at the treated microstructure tips when exposed to the appropriate reactants ($H_2O_2$).

Using alternating flows of aqueous acid or base in the bottom layer, the swelling and contraction of the pH-responsive hydrogel that surrounded the microstructures was controlled. In the top layer 0.5-1% hydrogen peroxide flowed in deionized water. On the tips of the microstructures the platinum catalyst was localized. As acid (an aqueous solution of HCl) flowed in the bottom layer, the hydrogel contracted, bending the microstructures away from the top layer. In this state, no bubbles were generated. When base (an aqueous solution of NaOH) was injected in the bottom layer, the hydrogel swelled, causing the microstructures to stand upright and exposing the platinum-covered tips to the top layer containing hydrogen peroxide. The contact of the catalyst (Pt) with the reactant ($H_2O_2$) generated the product, bubbles of oxygen, as can be seen in FIG. 16B. The volume of the gas generated from the Pt-catalyzed $H_2O_2$ decomposition was estimated from analysis (with Image J) of captured optical microscope images of the recorded video. This example demonstrates the ability of this device to utilize inorganic catalytic reactions, and pulses of gas, further expanding the scope of suitable chemical reactions.

Example 5

Capture and Release of a Biomolecule

To enable concerted hydrogel actuation and target molecule release in response to a single stimulus, a hydrogel and an aptamer were selected which both respond to changes in pH. The well-characterized aptamer against human α-thrombin, a serine protease that plays a key role in the blood-clotting cascade, was used. This aptamer is known to denature and lose thrombin affinity in response to low pH. Poly(acrylamide-co-acrylic acid), PAAc-co-PAAm is a well-studied hydrogel which changes volume phases in response to pH. In addition, the hydrogel has been extensively studied for a variety of biological and biomedical applications because of its biocompatibility and structural similarities to extracellular matrices. Therefore, by integrating the thrombin-binding aptamer and PAAc-co-PAAm hydrogel into SMARTS, the two pH-responsive components were able repetitively capture and release active thrombin selectively from a cocktail of molecules. Specifically, the microfluidic device incorporated flexible epoxy microstructures embedded in the pH-responsive hydrogel, immersed in two distinct aqueous fluid layers, separated by laminar flow, each with their own inlets and outlets. At the beginning of one sorting cycle, neutral pH in the bottom layer caused the hydrogel to swell, straightening the microstructures into the top layer. Introduction of acidic buffer into the bottom layer caused hydrogel contraction, which bent the microstructure tips into the bottom layer. Alternating the pH in the bottom solution layer alternately swelled or contracted the hydrogel, recycling the microstructure tips between the top and bottom layers of the device. When the microstructure tips were functionalized with a pH-sensitive, thrombin-specific aptamer, the actuating microstructures selectively captured thrombin flowing in the top layer and sequester and release it into the bottom acidic layer for collection and quantitative analysis. In this way, the microdevice can couple the pH-manipulated actuation and aptamer (un)folding with biomolecule catch-release, to separate specific molecules from a complex solution through the smoothly concerted action of the integrated materials.

Figure 17A:
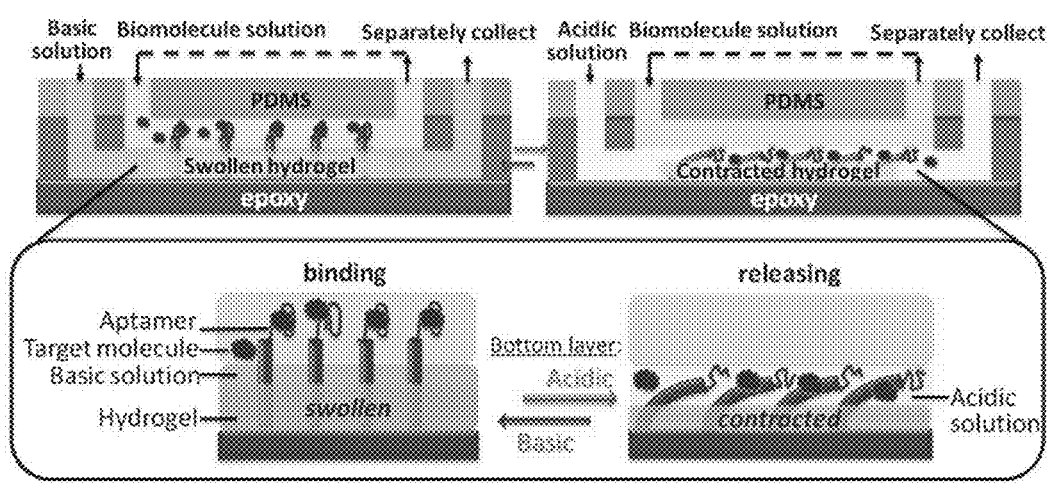
FIG. 17 is an illustration of a chemo-mechano-chemical ($C_1$-M-$C_2$) system according to one or more embodiments used in a specific binding reaction that selectively captures a biomolecule in the upper reactant layer and releases the biomolecule in the lower water layer; including (A) a schematic cross-section of the device, (B) an exploded view of the manufacture of the device and (C) A confocal image of the fabricated device taken at the branch point between the outlets for the top fluid layer (containing a fluorescein solution) and bottom fluid layer (containing a rhodamine B solution).
Figure 17B:
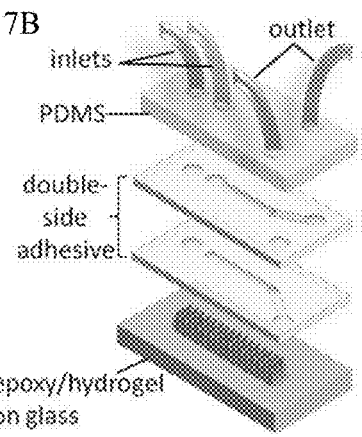
Figure 18:
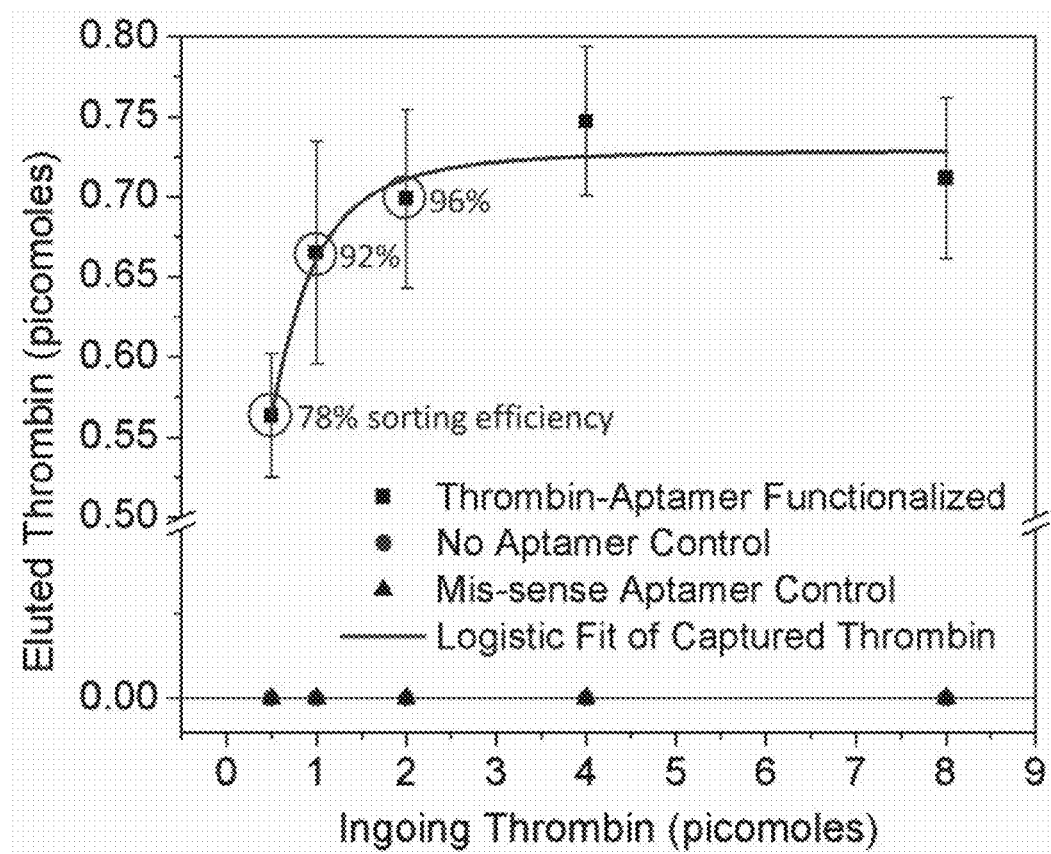
FIG. 18 is a plot showing the sorting capacity of aptamer-functionalized microdevice, defined as eluted thrombin/device capacity, shown for 0.5, 1 and 2 pmol of incoming thrombin.

Referring to FIGS. 17a and 17b, the microdevice employed separate inlets for the top and bottom layer to maintain separate control of the pH in each layer, which are separated within the device by constant laminar flow and can be a modification of the biphasic laminar flow system described with reference to FIG. 4. The device consisted of an array of epoxy fins 18 μm in height, 2 μm in depth, 10 μm long, with a pitch of 5 μm, which were UV-cured with polymerizing UVO-114 epoxy resin with 10 wt % glycidyl methacrylate from a negative PDMS mold of identical dimensions. The PDMS mold itself is cast from a silicon master. Subsequently, 2 uL of pH-sensitive poly(acrylamide-co-acrylic acid) hydrogel precursor solution (20% AAm, 20% AAc, 2% crosslinker bis-AAm and 1% UV-initiator Irgacure® 2959 by weight in deionized water) was then deposited on the epoxy structures and spread by gently placing an 18 mm×18 mm coverslip on top. The hydrogel was then UV-cured with a photomask that defines the channel area, 0.5 mm wide and 8 mm long rectangle, for about 7 minutes with a 100 mW/cm² lamp. Channels were formed by placing polyacrylic double-sided adhesive sheets with the same sized rectangle cut by laser cutter on top of the sample. The channels were subsequently capped with a polydimethylsiloxane sheet allowing integration with polyethylene tubing, creating two inlets each connected to a syringe pump, and two separate outlets.

Figure 17C:
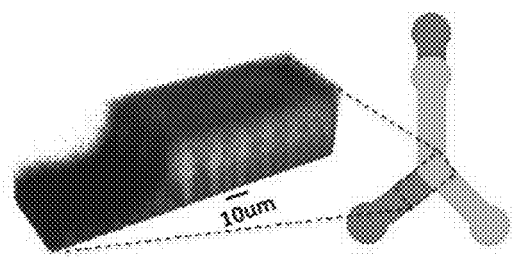

To enable separation of the target molecule from a complex ingoing mixture, the device utilizes distinct outlets for the top solution, containing the ingoing mixture, and the bottom solution, containing the released target molecule, which is illustrated in FIGS. 17a and 17b. Distinct inlets and outlets for the top and bottom layers were generated by stacking two different stickers which have a laser-cut channel and holes for tubing attachment (FIG. 17b). Specifically, the channel of microstructure epoxy fins (10 um width, 2 um length, 18 um height, 5um pitch) are surrounded by a stimuli-responsive hydrogel. The two layers of laser-cut stickers and a layer of PDMS are used to define the channel inlets and outlets and attached tubing is connected to a syringe pump. In order to collect two separate solutions, one that contains the sequestered molecule in the bottom and another that contains the rest of the mixture in the top, the microfluidic channel is designed branching into two outlets with a "Y"-shaped junction to divert the top and bottom-layer fluids to distinct collection outlets. Laminar flow maintains two distinct fluid layers that are collected in spatially separated outlets, as is illustrated in FIG. 17c. A syringe pump was used to inject two fluids through the tubing into the microfluidic channel with defined flow rates to maintain the top-bottom laminar flow.

The use of two separate outlets allowed for faster and more efficient sorting, as it did not require washing steps to remove non-target proteins or separate elution steps to release the captured thrombin. Instead, the dynamic response of the hydrogel to different pH solutions allowed for the concerted removal of the aptamer-bound thrombin from the top layer into the bottom layer in a single step. Moreover, the ability to continuously separate the target molecule from the top layer with the unique reversibility of the adaptively dynamic system allowed for the recycling of the ingoing solution for multiple rounds, allowing for separation of nearly all of the target molecules for high-sensitivity and high-efficiency biomolecule detection, isolation and purification.

For the best target capture, optimum thrombin-aptamer binding pH for the top fluid was determined. Therefore, the pH dependence of thrombin-aptamer binding using an ELONA immunoassay was tested. The highest thrombin-aptamer affinity was found to occur at pH 6.3, and thus this buffer was used in the top layer where the aptamer-thrombin binding occurs. A buffer with pH 7.2 was used in the bottom layer to swell the hydrogel and straighten the microstructures so that the aptamer-bearing tips would protrude into the top fluid, since PAAc-co-PAAm hydrogels swell at a pH>4.3, according to the pKa of the constituent acrylic acid groups in the hydrogel. Once the target molecule is captured by the aptamer in the top layer, the release of the target into the bottom layer occurs at an optimal pH at which the hydrogel contracts concurrently with the denaturation and reconfiguration of the aptamer, releasing the target molecule. pH values lower than 4.6 was found to give higher disassociation constant (Kd) and thus less binding. Since the hydrogel contracts at pH<4.3, a buffer with pH 3.2 was used for the bending and dissociating solution in the bottom layer.

The microfin tips were functionalized with aptamer by a stamping method. Briefly, a flat PDMS sheet inked with aptamer was placed on an $O_2$-plasma activated epoxy microfin tips overnight followed by thorough rinsing with pH 7.5 buffer. To examine the selective functionalization of the microstructure tips with aptamer as compared to the rest of the microstructure, a fluorophore-labeled oligonucleotide complementary to the aptamer was flushed into the microfluidic channel over the aptamer-bearing tips, in order to specifically label the aptamer with the dye and visualize it by fluorescent imaging. The red-colored tips indicated a good fidelity of selective functionalization and coverage of aptamer on the tips rather than the length of the microfins. To test whether the aptamer-functionalized microfins had an affinity for thrombin, DyLight dye-labeled thrombin was flowed through the microdevice when the aptamer-functionalized microstructures were extended into the top layer, allowing for aptamer-target molecule binding. Hydrogel contraction by flowing acidic solution in the bottom layer allowed for subsequent release of the thrombin from the microstructures into the bottom layer.

As the thrombin aptamer is known to selectively bind its target, the aptamer-functionalized device was also able to selectively capture thrombin from a mixture containing other serum proteins. To test the device's sorting selectivity, a solution containing thrombin and transferrin, an iron-binding plasma glycoprotein, was introduced into the microdevice. Two control devices were also tested identically, one of which was unfunctionalized and the other of which was functionalized with mutated thrombin aptamer not capable of binding thrombin. The resulting top and bottom fluids were collected and analyzed by PAGE gel. The thrombin-aptamer functionalized device selectively captured thrombin from the top fluid with binding-favored pH of 6.3. Subsequently, microstructures bent into the bottom fluid of dissociation-favored pH 3.2 successfully switched the aptamer into a non-binding state, thus effectively inducing significant release of thrombin in the bottom stream, while other proteins are well retained in the top layer. This shows the biocompatibility of the microdevice and more importantly its capability of programmable protein-type-specific binding and releasing. In contrast, control devices that were either unfunctionalized or functionalized with a known non-binding sequence retained thrombin in the top fluid with no release into the bottom fluid, which indicates the PAAm-co-PAAc hydrogel resists nonspecific binding. Overall, these results clearly show that the aptamer-functionalization of the device successfully imparts high specificity to the catch and release of target molecules from a mixture solution.

Further investigation demonstrated the effect of the device design on its capture and release capability for achieving optimum sorting efficiency. The regime for biomolecule transport through thus system consists of both convection in the direction of laminar flow and diffusion by Brownian motion. By calculating the Peclet number for the system, which would determine the relative dominance of convection to diffusion, the system is largely governed by convection: $Pe=Q/(wD)$, where Q is the fluid flow rate, w is the channel width, and D is the diffusion coefficient of the biomolecule. Q is determined by the minimum flow rate set by the syringe pump necessary to maintain laminar flow in the biphasic system, 10 4/min; w is the channel width defined as 500 μm; D for thrombin is taken to be 87 $μm^2$/s. Thus, the Peclet number for flow in the microdevice is 3,831, signifying that convective forces play a more dominant role than Brownian motion. As such, enhancing diffusional transport of the biomolecule to the surface-bound aptamer by decreasing the channel height would not be as significant in the system as it would in a Brownian motion-dominated system. However, decreasing the flow rate further increases the amount of time a given target molecule occupies the device, and therefore increases the probability of target capture by diffusion to the surface. Therefore, altering the dimensions of the device by increasing the area and decreasing the height could enable greater capture of target molecules as long as laminar flow could be maintained at lower fluid flow rates.

Based on the device with dimensions of 0.5 mm (width)×8 mm (length)×0.06 mm (height), we measured its capture capacity by flowing in increasing amounts of thrombin in the ingoing solution until the amount of captured and released thrombin in a single cycle was saturated. It was observed that the amount of released thrombin increased with increasing ingoing thrombin up to 0.725 picomoles of thrombin, and thus that this was the maximum binding capacity of the device (see FIG. 18). The sorting efficiency of a microdevice was thus defined as the amount of target molecule captured in one actuation cycle vs. the empirical binding capacity of the device. This dimension-defined sorting efficiency, was calculated for ingoing thrombin solutions of 0.5 picomoles, 1 picomoles, and 2 picomoles, and shows that the capture efficiency tends towards 1 as the concentration of the target molecule in the ingoing solution is increased beyond the device capacity.

Figure 19:
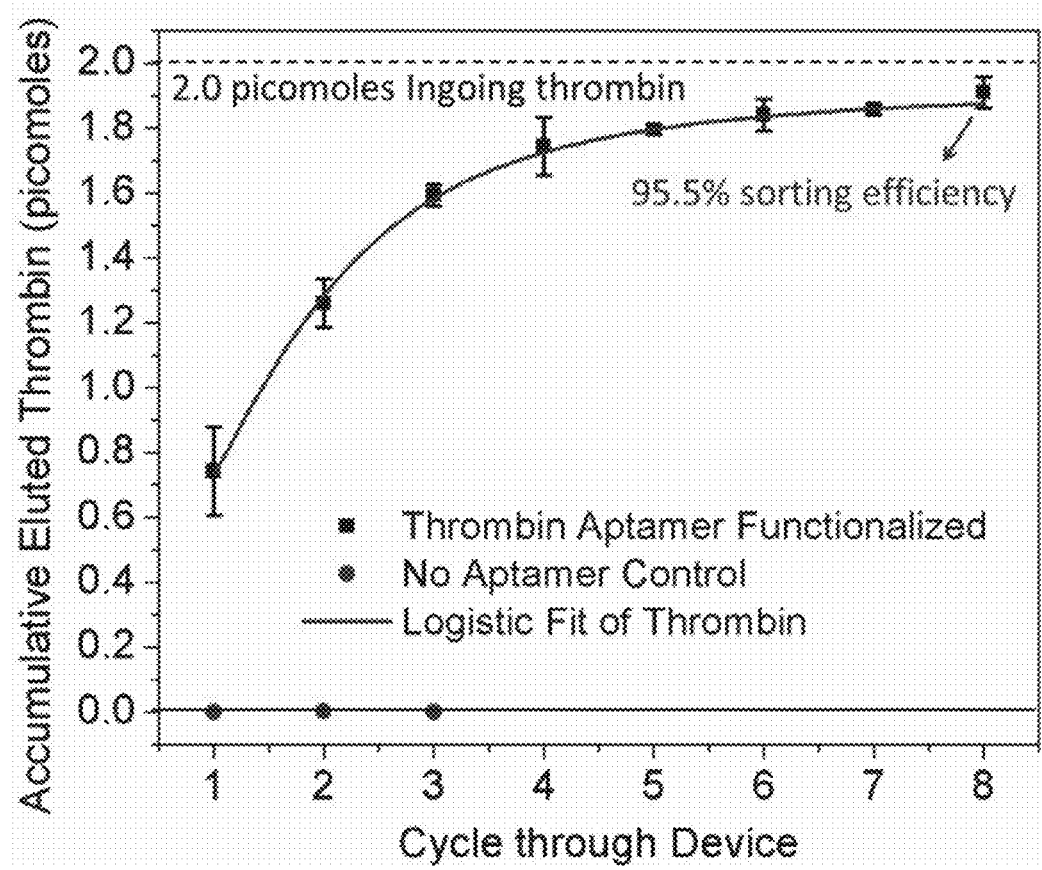
FIG. 19 is a plot of the amount of thrombin collected form recycling ingoing solutions and demonstrating the cumulative effect of eluted thrombin after each actuation.

For applications in which maximum target molecule recovery is required, the device's sorting capacity was expanded by recycling the same solution through multiple capture and release cycles. Recycling the ingoing solution compensates for the thrombin that was not captured in each cycle due to equilibrium dynamics or convective flow over the aptamer bound to the surface. When a solution initially containing 2 pmol thrombin was recycled through the device, we observed that after 8 cycles through the device, 95.5% of the initial thrombin was recovered, as illustrated in FIG. 19. This clearly demonstrates the robustness of the microdevice towards repeated catch-and-release cycles. Furthermore, the near quantitative recovery of the ingoing thrombin suggests that the microdevice has little nonspecific association with the target protein. In contrast, an unfunctionalized device did not show any thrombin released in the bottom stream, even after multiple actuation cycles.

In summary, the microdevice uniquely couples pH-manipulated actuation and aptamer (un)folding with biomolecule catch-release, allowing for the non-destructive separation of specific molecules from a complex solution through the smoothly concerted actions of a hydrogel-embedded microstructure functionalized with aptamer in biphasic fluid. Additionally, the unique reversibility of hydrogel swelling and aptamer folding allows for repeated processing of a single input solution, enabling the reusable dynamic system to capture almost all (95.5%) of the target molecules from initial mixture. The dynamic non-destructive protein catch and release controlled by programmed actuation makes this platform fundamentally unique and suitable for numerous biological and biomedical applications that require separation of sub-microliter samples for downstream analysis with low turnaround time. The variability and tunability of the two key components, hydrogel and aptamer, together with the geometry and material of the microstructure, render the integrated microdevices a broad-based form for wide applications. The microstructures can be functionalized with a diverse array of aptamers, antibodies, proteins, or small molecules, allowing capture and possible further analysis of almost any target molecule including small organic or inorganic molecules, nucleic acids, proteins, or intact cells. Furthermore, the response of the hydrogel can be tuned to achieve various stimuli-responsive sorting as hydrogels can be made to respond to not only pH, but to temperature, light, electric/magnetic field, ionic concentration, etc. Such an adaptively dynamic system could find further applications in biomolecule separation, purification, concentration, detection, and isolation.

Measuring the Presence of Aptamer on Microstructure Tips with Complementary Oligonucleotide:

The complementary sequence of the thrombin aptamer conjugated to a Cy5 fluorophore was diluted in deionized water and flowed through the microdevice with microstructures functionalized with the thrombin-binding aptamer at a rate of ~10 µL/min with a syringe pump. Unbound complementary strands were washed with deionized water and subsequently pH 7.2 10×PBS buffer. The fluorescence of the bound complementary strands was viewed under the confocal microscope at an excitation/emission of 543/633 nm wavelength.

ELONA assay for pH dependence of aptamer-thrombin binding: ELONA/immunoassay experiments were carried out in which 50 nM biotinylated DNA aptamer was immobilized on a streptavidin-coated plate using 1×PBS, pH 7.4 for 30 min at 37° C. After washing with PBS-Tween20, PBS-casein blocking buffer was applied overnight. Subsequently, thrombin concentrated at 500 nM down to 2 nM was deposited and left to incubate for 50 min at room temperature. After another wash with PBS-Tween20, pH buffers of pH 3.2, 4.6, 6.3, 7.2, and 8.7 were applied and incubated for 30 min, after which another round of PBS-Tween20 washes were applied. In order to measure the amount of thrombin bound to the immobilized aptamer, anti-thrombin HRP conjugate was deposited and incubated for one hour, after which a solution of TMB and $H_2O_2$ was added and the color development at 650 nm was measured for 10 minutes. After 20 minutes, HCl was added and absorbance at 450 nm was measured. The absorbance intensity was plotted as a function of thrombin concentration for each pH used. While the inflection of these curves reflect the Kd constant of thrombin-aptamer binding, the apparent Kd between the surface-immobilized aptamer and thrombin was estimated at each pH by linearizing the data of absorbance as a function of thrombin concentration according to the procedure described by Ovadi, et al (Károly Liliom, Ferenc Orosz, Lóránt Horváth & Ovádi, J. Quantitative evaluation of indirect ELISA effect of calmodulin antagonists on antibody binding to calmodulin. Journal of Immunological Methods 143, 119-125 (1991)). The apparent Kd is estimated as the inverse slope of the linearized plots.

PAGE Experiment for Selectivity Test:

Loading controls and fractions from the top and bottom layers of the device were collected and pooled after several actuations conducted upon an ingoing solution containing 20 nM of thrombin and 20 nM transferrin. Fractions were concentrated by lyophilization, redissolved in 1×NuPAGE protein loading buffer (Invitrogen), heated to 95° C. for 5 minutes and analyzed by electrophoresis (12% NuPAGE gel (Invitrogen), 200V, 45 min) The gel was subsequently stained with Sypro Ruby (Sigma) and imaged on a Chemilmager.

ELISA Experiment for Quantitative Measurement of Thrombin Concentration:

To measure the amount of thrombin eluted from the top and bottom layer of the microdevice, a thrombin-specific ELISA kit was used. Standard curves were made of thrombin at known concentrations in the relevant pH buffers, pH 6.3 and pH 3.2. Aliquots of collected solution from the top and bottom layer were diluted appropriately and dispensed along with the standard solutions onto a microplate pre-coated with a monoclonal antibody specific for thrombin. After incubation of the thrombin solutions for 2 hours, the unbound thrombin was washed away. A biotinylated polyclonal antibody specific for thrombin was then incubated on the microplate for 1 hour. After washing away excess, unbound thrombin-specific antibody, streptavidin peroxidase conjugate was deposited on the microplate to recognize the bound thrombin-specific antibody and left to incubate for 30 minutes. After washing away excess streptavidin peroxidase conjugate, a chromogen substrate consisting of a peroxidase enzyme was added to the microplate and the blue color allowed to develop for about 10 minutes before an acidic stopping solution was added and the color at 450 nm is measured for each well by a well-plate reader. In this way the color of the collected solutions were compared to the standard curve and the corresponding amount of thrombin calculated.

It will be appreciated that while a particular sequence of steps has been shown and described for purposes of explanation, the sequence may be varied in certain respects, or the steps may be combined, while still obtaining the desired configuration. Additionally, modifications to the disclosed embodiment and the invention as claimed are possible and within the scope of this disclosed invention. A variety of gel formulations and chemical reactions (in the broad sense, as described earlier) can be utilized.

Example 6

Exothermic Catalytic Processes Using Cumene Hydroperoxide Decomposition and "Click" Reaction Between Octyl Azide and Phenylacetylene To demonstrate the wide scope of the SMARTS platform and its applicability to a variety of chemical reactions as the source of continuous, autonomous homeostatic function (CM), different types of exothermic catalytic reactions were investigated and the resulting self-regulation of the temperature in the device was studied. SMARTS utilizing cumene hydroperoxide (40% in toluene) decomposition catalyzed by triphenylcarbenium hexafluorophosphate, compared to the one utilizing neat hydrosilylation reaction of 1-hexene with triethylsilane, presents a shorter initial oscillation period (3.28 min/cycle) and larger amplitudes in both temperature (4.6° C., 30.0-34.6° C.) and actuation (~6 μm, tip position Z=~9-15 μm). For SMARTS with cumene hydroperoxide decomposition, the microfins with tips functionalized with triphenylcarbenium hexafluorophosphate were immersed in 4.0 μL 40% (vol./vol.) cumene hydroperoxide in toluene in the top phase and 1 μL DIW in the bottom phase.

The neat "click" reaction between octyl azide and phenylacetylene catalyzed by $Cu(PPh_3)_2NO_3$ shows similar behavior, with a shorter initial oscillation period (3.45 min/cycle) and larger amplitudes in both temperature (3.6° C., 30.6-34.2° C.) and actuation (~5 um, tip position Z=~9-14 μm). The observation and detailed analysis of the progresses of these devices were stopped after one hour while they were still running. For SMARTS with "click" reaction, the microfins with tips functionalized with nitratobis(triphenylphosphine)copper(I) were immersed in 4.0 μL 1:1 (by mol) octyl azide (2.5 μL) and phenylacetylene (1.5 μL) in the top phase and 1 μL DIW in the bottom phase.

Figure 21B:
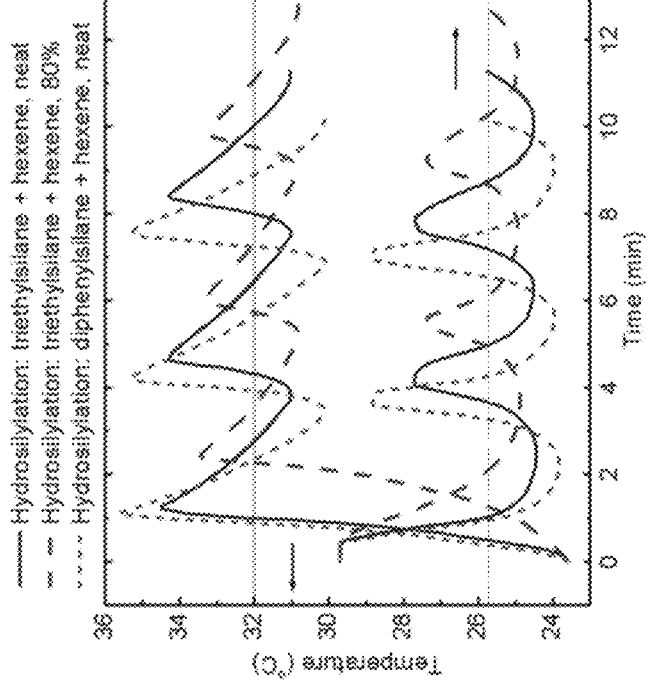

FIG. 21B provides graphs showing the time-resolved temperature and vertical projection (Z) of the tips of microfins embedded in a hydrogel of pNIPAAm, using cumene hydroperoxide (40% in toluene) decomposition catalyzed by triphenylcarbenium hexafluorophosphate, and a "click" reaction between octyl azide and phenylacetylene (neat) catalyzed by nitratobis(triphenylphosphine)copper(I), in comparison with the behavior of SMARTS with 1-hexene: triethylsilane (neat). The straight horizontal lines, indicate the LCST of hydrogel and the position of the liquid interface.

Example 7

Effect of the System Geometry

Figure 22A:
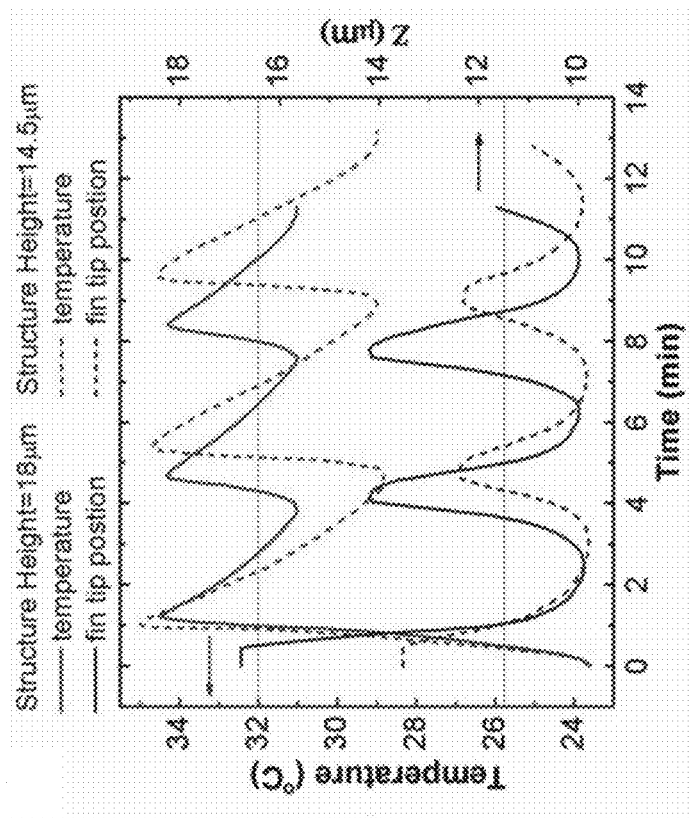
FIG. 22 shows the effect of the SMARTS geometry on the homeostatic characteristics, in which (a) shows self-oscillation behavior of SMARTS having different liquid interface heights and (b) shows the self-oscillation behavior of SMARTS having different microstructure dimensions.

To study the correlation of the homeostatic performance and the liquid interface position, the bilayer interface height was raised from ~12 μm to ~15 μm by increasing the amount of water by 1.3 μL, while keeping other conditions the same. With the higher interface, the microfins oscillate around the new interface level of ~15 μm with a smaller amplitude (~2 um, tip position Z=~14-16 μm), compared to its original amplitude of ~4 um, as shown in FIG. 22A (The time-resolved temperature and vertical projection (Z) of the tips of microfins embedded in a hydrogel of pNIPAAm, with liquid interface at a height of ~15 μm from the base of the microfins, in comparison with the original interface at ~12 μm). The straight horizontal lines indicate the LCST of hydrogel and the ~12- and ~15-μm-high liquid interfaces. Importantly, the temperature oscillations are smoothened (1.7° C. amplitude) around a lower homeostatic point (32.0° C.), compared to the original homeostasis around 32.7° C. with fluctuation in the range of 3.2° C. when the liquid interface is ~12 μm high. This demonstrates the controllability of the homeostatic function by varying one easily-tunable parameter—the position of the liquid interface.

Example 8

Varied Microstructure Dimensions

Figure 22B:
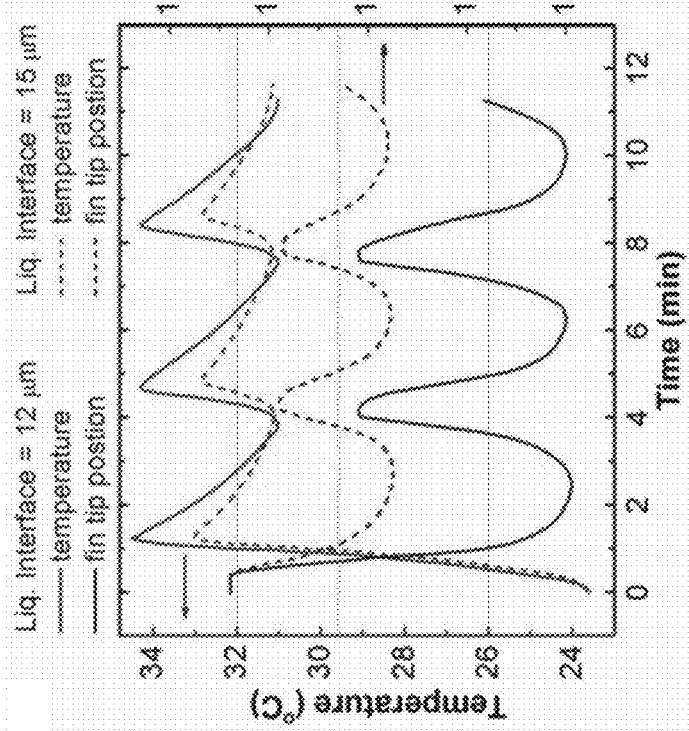

To study the correlation of the homeostatic performance and microstructure dimensions, 14.5-μm-tall microfins (with other dimensions matching the original 18.0-μm-tall structures) were used in SMARTS. With the smaller aspect ratio of the shorter fins, the actuation slows down and the oscillation period increases to 3.80 min/cycle (from 3.58 min/cycle), as shown in FIG. 22B (The time-resolved temperature and vertical projection (Z) of the tips of microfins embedded in a hydrogel of pNIPAAm, with 14.5-μm-tall microfins, in comparison with those of the original 18.0-μm-tall ones). The straight horizontal lines indicate the LCST of hydrogel and the ~12-μm-high liquid interface. Reducing fin height, while keeping the liquid interface constant, means higher relative height of the interface for the shorter fin, therefore the actuation amplitude decreases to ~2 μm around a lower level of ~11 μm, however the temperature amplitude increases to 5° C. between 30.2-35.2° C., in agreement with a higher effective stiffness of shorter fins.

Example 9

Control Experiments without Catalyst

When a control sample carrying no catalyst on the microstructures was externally heated above LCST (to 34.1° C.), the system simply cooled down to room temperature (22.0° C.) in ~8.8 min, not being able to maintain the temperature, in stark contrast to the samples with catalyst, which showed excellent homeostatic capability. The similar initial slope observed in the control sample without a catalyst to those of the functioning samples indicates that the reaction occurring in SMARTS switches off almost as soon as the fins bend across the liquid interface. At the end of the reaction lifetime, the homeostatic SMARTS cool down much slower than the control system (~50 min compared to the 8.8 min for the control sample without a catalyst). This observation indicates that at the end of the lifetime when fins remained in the upright configuration, the reaction was still going on and consuming the remainder of the reagents, but was not anymore producing enough heat to reach the LCST of the gel and induce the next oscillation cycle.

Upon review of the description and embodiments of the present invention, those of skill in the art will understand that modification and equivalent substitutions may be performed in carrying out the invention without departing from the essence of the invention. Thus, the invention is not meant to be limited by the embodiments described explicitly above, and is set forth in the claims which follow.

What is claimed is:

1. A method of chemo-mechano-chemical ($C_1$-M-$C_2$) actuation, comprising:
   (a) providing a chemo-mechano-chemical ($C_1$-M-$C_2$) system comprising:
   a base supporting an actuatable structure, said structure comprising a functionalized portion and being embedded in an environmentally responsive gel capable of volume change in response to an environmental stimulus;
   a first fluid layer disposed over the base and in contact with the actuatable structure, said first fluid layer comprising the environmentally responsive gel; and
   a second fluid layer in contact with the actuatable structure, wherein the first and second fluid layers are positioned such that the functionalized portion is in contact with the second fluid layer in a first relaxed state and in contact with the first fluid layer in a second actuated state and wherein the functionalized portion interacts with at least one of the layers to provide a chemical or physical response; and
   (b) exposing the system to a stimulus, wherein the actuatable structure moves from the first relaxed position in which the functionalized portion is in contact with the second fluid layer to the second actuated position in which the functionalized portion is in contact with the first fluid layer,
   wherein the functionalized portion undergoes a chemical reaction with at least one component of one of the first and second fluid layers, and
   wherein the system reversibly actuates and triggers the chemical reaction $C_2$ in response to the stimulus, to thereby provide a feedback loop.

2. The method of claim 1, wherein the chemical or physical response provides the environmental stimulus that triggers a volume change in the environmentally responsive gel so that the system is self-regulating.

3. The method of claim 1, wherein the stimulus triggers a volume change in the environmentally responsive gel.

4. The method of claim 3, wherein the second fluid is a gas and the chemical or physical response takes place in the first fluid.

5. The method of claim 1, wherein the first and second fluid layers are vertically arranged.

6. The method of claim 1, wherein the first and second fluid layers are horizontally arranged.

7. The method of claim 1, wherein the gel is a hydrogel, a lyogel or an organogel.

8. The method of claim 1, wherein the stimulus is one or more from the following parameters: pH, heat, light, electric field, ultrasound, magnetic field, pressure, ion concentration, organic molecule concentration, biomolecule concentration or a combination thereof.

9. The method of claim 1, wherein the first and second fluid layers are arranged in a static configuration.

10. The method of claim 1, wherein the system comprises a microfluidic system and the first and second fluids flow in laminar pathways through the structures embedded in the environmentally responsive gel.

11. The method of claim 1, wherein the functionalized portion comprises a catalyst and one of the first or second fluid layers comprises reagents that react when brought in contact with the catalyst.

12. The method of claim 1, comprising selecting the gel, the structure and functionalized portion to provide a preselected actuation characteristic.

13. The method of claim 1, wherein the structures comprise a first upper portion comprising a first reactant and a second lower portion comprising a second reactant, wherein the structures are positioned and arranged such that the structures are spaced apart in the first relaxed state and the first and second reactants of neighboring structures contact each other in the second actuated state bringing the first and the second reactant in contact to provide a chemical or physical response.

14. The method of claim 1, wherein the system comprises a first set of structures comprising a first reactant and a second set of structures comprising a second reactant, wherein the structures are positioned and arranged such that the first set and second set of structures are spaced apart in the first relaxed state and the first and second reactants of neighboring first and second set of structures contact each other in the second actuated state to provide a chemical or physical response.

15. The method of claim 1, wherein the system further comprises a third reaction layer disposed between the first layer comprising the environmentally responsive gel and the second layer comprising the functionalized portion in the first relaxed state, wherein the third reaction layer comprises reactants capable of being catalyzed by the functionalized portion to provide a chemical or physical response.

16. The method of claim 1, wherein the system couples the mechanical action of a temperature-responsive gel with temperature generation occurring as the chemical or physical response to provide the feedback loop.

17. The method of claim 1, wherein the functionalized portion comprises an enzyme and the enzyme interacts with at least one of the fluid layers to provide a biochemical response.

18. The method of claim 1, wherein the functionalized portion comprises a dye and the dye is moveable between the first and second fluid layers to reversibly display or quench the dye.

19. The method of claim 1, wherein the functionalized portion comprises an aptamer and the aptamer is movable between the first and second fluid layers to reversibly bind and release a target molecule.

20. A method of maintaining a temperature within a preselected range; comprising:
   (a) providing a chemo-mechano-chemical($C_1$-M-$C_7$) system, comprising:
   a base supporting an actuatable structure, said structure comprising a functionalized portion and being embedded in an environmentally responsive gel capable of volume change in response to an environmental stimulus;
   a first fluid layer disposed over the base and in contact with the actuatable structure, said first fluid layer comprising the environmentally responsive gel; and
   a second fluid layer in contact with the actuatable structure, wherein the first and second fluid layers are positioned such that the functionalized portion is in contact with the second fluid layer in a first relaxed state and in contact with the first fluid layer in a second actuated state and wherein the functionalized portion interacts with at least one of the layers to provide a chemical or physical response; and
   (b) exposing the system to a stimulus, wherein the actuatable structure moves from the first relaxed position in which the functionalized portion is in contact with the second fluid layer to the second actuated position in which the functionalized portion is in contact with the first fluid layer,
   wherein the functionalized portion undergoes a chemical reaction with at least one component of one of the first and second fluid layers to generate a change in temperature, and
   wherein the temperature of the chemo-mechano-chemical ($C_1$-M-$C_2$) system is maintained within a preselected range.

21. The method of claim 20, wherein the change in temperature due to an exothermic reaction.

22. The method of claim 20, wherein the change in temperature due to an endothermic reaction.

23. The method of claim 20, wherein the analytes are selected from the group consisting of aptamer, protein, pathogen, antibody, biomolecule, organic molecule, inorganic molecule or ion, and cell.

* * * * *

SEQUENCE LISTING

<160> NUMBER OF SEQ ID NOS: 2

<210> SEQ ID NO 1
<211> LENGTH: 10
<212> TYPE: DNA
<213> ORGANISM: Artificial Sequence

```
-continued

<220> FEATURE:
<221> NAME/KEY: source
<223> OTHER INFORMATION: /note="Description of Artificial Sequence:
      Synthetic oligonucleotide"

<400> SEQUENCE: 1
tttttttttt                                                                 10

<210> SEQ ID NO 2
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
atctaactgc tgcgccgccg ggaaaatact gtacggttag attttttttt t                   51
```